United States Patent
Konishi et al.

(10) Patent No.: US 10,869,828 B2
(45) Date of Patent: *Dec. 22, 2020

(54) COSMETIC

(71) Applicant: SHIN-ETSU CHEMICAL CO., LTD., Tokyo (JP)

(72) Inventors: Masayuki Konishi, Tokorozawa (JP); Chihiro Hayakawa, Yokohama (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/314,896

(22) PCT Filed: Apr. 26, 2017

(86) PCT No.: PCT/JP2017/016450
§ 371 (c)(1),
(2) Date: Jan. 3, 2019

(87) PCT Pub. No.: WO2018/008238
PCT Pub. Date: Jan. 11, 2018

(65) Prior Publication Data
US 2019/0201317 A1 Jul. 4, 2019

(30) Foreign Application Priority Data
Jul. 4, 2016 (JP) ................. 2016-132388

(51) Int. Cl.
A61K 8/25 (2006.01)
A61K 8/898 (2006.01)
A61Q 1/10 (2006.01)
A61Q 1/12 (2006.01)
A61Q 3/02 (2006.01)
A61Q 5/06 (2006.01)
A61Q 15/00 (2006.01)
(Continued)

(52) U.S. Cl.
CPC .............. *A61K 8/898* (2013.01); *A61Q 1/02* (2013.01); *A61Q 1/06* (2013.01); *A61Q 1/08* (2013.01); *A61Q 1/10* (2013.01); *A61Q 1/12* (2013.01); *A61Q 3/02* (2013.01); *A61Q 5/06* (2013.01); *A61Q 5/12* (2013.01); *A61Q 15/00* (2013.01); *A61Q 17/04* (2013.01); *A61Q 19/00* (2013.01); *A61Q 19/08* (2013.01)

(58) Field of Classification Search
None
See application file for complete search history.

(56) References Cited

U.S. PATENT DOCUMENTS

2009/0035335 A1* 2/2009 Marotta ............... A61K 8/73
424/401
2015/0315213 A1 11/2015 Chang et al.
2017/0327605 A1 11/2017 Hagiwara

FOREIGN PATENT DOCUMENTS

EP 3 246 342 A1 11/2017
JP S52-102889 A 8/1977
(Continued)

OTHER PUBLICATIONS

Kengo Arai et al: "Reason for the High Solubility of Chemically Modified Poly(vinyl alcohol)s in Aqueous Solution", Macromolecules, vol. 48, No. 5, 10, pp. 1573-1578.
(Continued)

*Primary Examiner* — Susan T Tran
(74) *Attorney, Agent, or Firm* — Oliff PLC

(57) ABSTRACT

A cosmetic containing an organosiloxane graft polyvinyl alcohol polymer having a structural unit shown by the general formula (1) and a structural unit shown by the general formula (3). The organosiloxane graft polyvinyl alcohol polymer has a number average molecular weight (Mn) of 5,000 to 500,000 as measured by GPC. There can be provided a cosmetic which has favorable feeling on use and oil resistance, and which is excellent in cosmetic durability improvement.

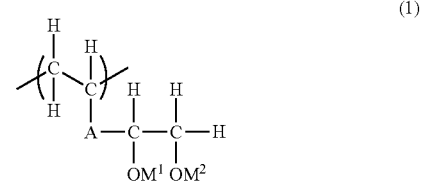

(1)

where $M^1$ and $M^2$ each represent a hydrogen atom, an acetyl group, or a siloxane group shown by the general formula (2), provided that at least one of $M^1$ and $M^2$ is a siloxane group shown by the general formula (2); and A represents a single bond or a linking group,

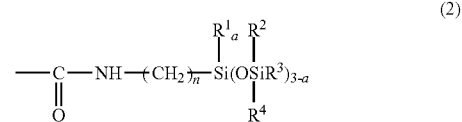
(2)

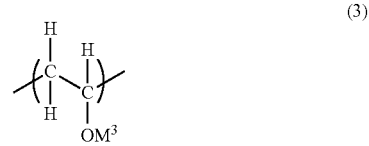

(3)

where $M^3$ represents a hydrogen atom, an acetyl group, or a siloxane group shown by the formula (2).

4 Claims, 1 Drawing Sheet

(51) Int. Cl.
*A61Q 17/04* (2006.01)
*A61Q 1/08* (2006.01)
*A61Q 1/02* (2006.01)
*A61Q 19/00* (2006.01)
*A61Q 5/12* (2006.01)
*A61Q 1/06* (2006.01)
*A61Q 19/08* (2006.01)

(56) References Cited

FOREIGN PATENT DOCUMENTS

| | | |
|---|---|---|
| JP | S55-164614 A | 12/1980 |
| JP | H02-025411 A | 1/1990 |
| JP | H04-045155 A | 2/1992 |
| JP | H06-116390 A | 4/1994 |
| JP | H07-196449 A | 8/1995 |
| JP | 2007-261995 A | 10/2007 |
| JP | 2011-246642 A | 12/2011 |
| JP | 2012-197265 A | 10/2012 |
| JP | 2016-501948 A | 1/2016 |
| WO | WO-2018008238 A1 * 1/2018 ............... A61Q 1/08 |

OTHER PUBLICATIONS

Feb. 4, 2020 Extended European Search Report issued in European Patent Application No. 17823846.5.
Jul. 18, 2017 International Search Report issued in International Patent Application No. PCT/JP2017/016450.

* cited by examiner

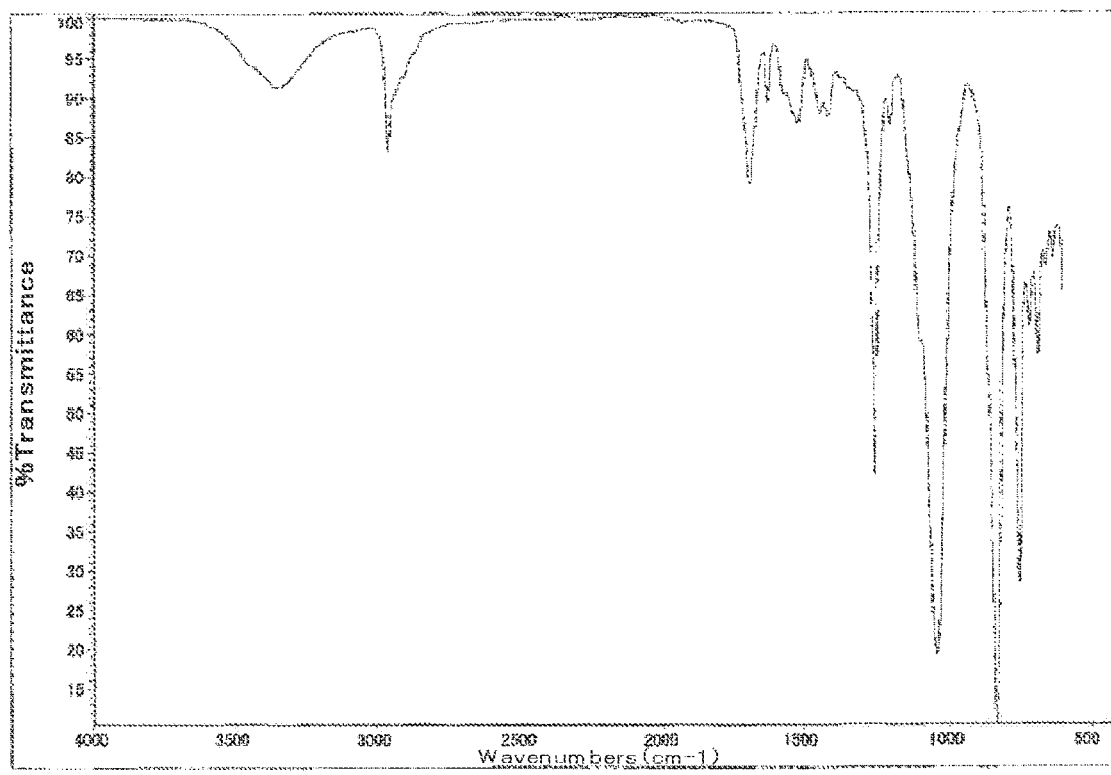

COSMETIC

TECHNICAL FIELD

The present invention relates to a cosmetic. It is to be noted that, herein, a composition for cosmetic (cosmetic composition) is sometimes simply referred to as cosmetic.

BACKGROUND ART

In order to improve cosmetic durability, for example, a film-forming polymer is widely blended. Particularly, regarding make-up cosmetics, sunscreen cosmetics, and so forth, there are demands for the development of products which are excellent in water resistance, oil resistance (sebum resistance) and sweat resistance. Hence, trimethylsiloxysilicate, silicone-modified acrylic polymers, and the like have been used.

However, when a cosmetic is blended with a large amount of hard film formed from such trimethylsiloxysilicate, the cosmetic provides unfavorable tactile feel and rough feeling after the application. Moreover, since the film is brittle, the film is cracked when stress is applied thereto. This brings about problems such as excessively dried skin condition in use. To compensate for these disadvantages, there has been proposed a composition which uses the aforementioned silicone resin in combination with dimethyl polysiloxane having high polymerization degree (Patent Literature 1). Nevertheless, these film formers become sticky due to dimethyl polysiloxane having high polymerization degree, and sufficient oil resistance is not obtained.

On the other hand, a silicone-modified acrylic polymer forms a soft and highly adhesive film, and can impart smooth touch, glossiness, and so forth to a cosmetic containing this film (Patent Literature 2). However, the film formed by using such a silicone-modified acrylic polymer is not satisfactory due to weak strength and likelihood of makeup deterioration. Meanwhile, there has also been proposed a composition which uses a combination of the silicone resin and silicone-modified acrylic polymer (Patent Literature 3). However, the composition of these does not have sufficient oil resistance and is not effective in improving cosmetic durability.

Moreover, Patent Literature 4 provides a substituted silylalkyl carbamate polyvinyl alcohol as a material that has general characteristics of polyvinyl alcohol such as film-forming property, toughness, excellent gas barrier property, and transparency as well as characteristics of silicone having a branched structure such as high solubility with respect to an organic solvent and excellent handleability as a liquid material. However, since a usual polyvinyl alcohol has low reactivity with a silicone modifying agent, an excessive amount of the silicone modifying agent is required to obtain the substituted silylalkyl carbamate polyvinyl alcohol with high modification rate, thereby increasing the production cost. Thus, this material is unsuited for cosmetic usage in many cases.

CITATION LIST

Patent Literatures

Patent Literature 1: Japanese Unexamined Patent Application Publication No. Hei 4-45155
Patent Literature 2: Japanese Unexamined Patent Application Publication No. Hei 2-25411
Patent Literature 3: Japanese Unexamined Patent Application Publication No. Hei 7-196449
Patent Literature 4: Japanese Unexamined Patent Application Publication No. 2011-246642

SUMMARY OF INVENTION

Technical Problem

The present invention has been made in view of the above situation. An object of the present invention is to provide a cosmetic which has favorable feeling on use and oil resistance, and which is excellent in cosmetic durability improvement.

Solution to Problem

To achieve the above object, the present invention provides a cosmetic comprising an organosiloxane graft polyvinyl alcohol polymer comprising: a structural unit shown by the following general formula (1), and a structural unit shown by the following general formula (3),
wherein the organosiloxane graft polyvinyl alcohol polymer has a number average molecular weight (Mn) of 5,000 to 500,000 as measured by GPC in terms of polystyrene,

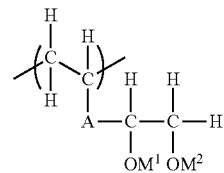

(1)

wherein $M^1$ and $M^2$ each represent a hydrogen atom, an acetyl group, or a siloxane group shown by the following general formula (2), provided that at least one of $M^1$ and $M^2$ is a siloxane group shown by the general formula (2); and A represents a single bond or a linking group,

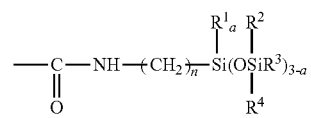

(2)

wherein $R^1$ represents a monovalent organic group having 1 to 6 carbon atoms; $R^2$, $R^3$, and $R^4$ each represent a monovalent organic group having 1 to 6 carbon atoms or a siloxy group shown by —$OSiR^5R^6R^7$, where $R^5$, $R^6$, and $R^7$ each represent a monovalent organic group having 1 to 6 carbon atoms; "n" represents an integer of 1 to 10; and "a" represents an integer of 0 to 2,

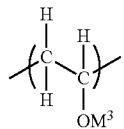

(3)

wherein $M^3$ represents a hydrogen atom, an acetyl group, or a siloxane group shown by the general formula (2).

In the organosiloxane graft polyvinyl alcohol polymer blended in the inventive cosmetic, decreasing the high crystallinity of the polyvinyl alcohol increases the solubility to an organic solvent and increases the reactivity with a modifying agent. Such a polymer is an inexpensive and excellent material that has general characteristics of polyvinyl alcohol such as film-forming property and transparency as well as characteristics of silicone having a branched structure such as high solubility with respect to an organic solvent and excellent handleability as a liquid material. Therefore, the polymer can be suitably used as a film former for cosmetic, and can also be used as an emulsification aid, a dispersant, and a lipophilic thickener. The cosmetic blended with such a polymer has favorable feeling on use and oil resistance and is excellent in cosmetic durability improvement.

In the general formula (2), preferably, "n" is 3, $R^2$, $R^3$, and $R^4$ are methyl groups, and "a" is 0.

In the case where "n" is 3, $R^2$, $R^3$, and $R^4$ are methyl groups, and "a" is 0 in the general formula (2) as described above, the polymer is more excellent in productivity, reactivity, and the like.

Moreover, the organosiloxane graft polyvinyl alcohol polymer is preferably a reaction product of a (butenediol/vinyl alcohol) copolymer and tristrimethylsiloxysilylpropyl isocyanate.

As described above, the organosiloxane graft polyvinyl alcohol polymer blended in the inventive cosmetic is preferably a reaction product between a (butenediol/vinyl alcohol) copolymer and tristrimethylsiloxysilylpropyl isocyanate.

Advantageous Effects of Invention

The organosiloxane graft polyvinyl alcohol polymer blended in the inventive cosmetic has film-formation ability to give a tough and soft film. Hence, the inventive cosmetic blended with this polymer achieves cosmetic durability improvements in terms of cosmetic secondary adhesion, peeling off, and the like. The cosmetic has favorable feeling on use (touch) and oil resistance.

BRIEF DESCRIPTION OF DRAWING

FIG. 1 is a graph showing an IR analysis result of a polymer obtained in Production Example 1.

DESCRIPTION OF EMBODIMENTS

As described above, there have been demands for a cosmetic having favorable feeling on use and oil resistance and being excellent in cosmetic durability improvement.

The present inventors have earnestly studied to achieve the above-described object. As a result, the inventors have found that when a cosmetic contains an organosiloxane graft polyvinyl alcohol polymer which has a structural unit shown by the following general formula (1) and a structural unit shown by the following general formula (3), and which has a number average molecular weight (Mn) of 5,000 to 500,000 as measured by GPC in terms of polystyrene, the cosmetic has favorable feeling on use and excellent oil resistance. This finding has led to the completion of the present invention.

Specifically, the present invention is a cosmetic comprising an organosiloxane graft polyvinyl alcohol polymer comprising: a structural unit shown by the following general formula (1), and a structural unit shown by the following general formula (3), wherein the organosiloxane graft polyvinyl alcohol polymer has a number average molecular weight (Mn) of 5,000 to 500,000 as measured by GPC in terms of polystyrene,

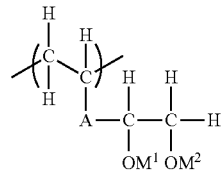

(1)

wherein $M^1$ and $M^2$ each represent a hydrogen atom, an acetyl group, or a siloxane group shown by the following general formula (2), provided that at least one of $M^1$ and $M^2$ is a siloxane group shown by the general formula (2); and A represents a single bond or a linking group,

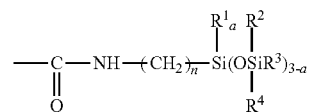

(2)

wherein $R^1$ represents a monovalent organic group having 1 to 6 carbon atoms; $R^2$, $R^3$, and $R^4$ each represent a monovalent organic group having 1 to 6 carbon atoms or a siloxy group shown by $-OSiR^5R^6R^7$, where $R^5$, $R^6$, and $R^7$ each represent a monovalent organic group having 1 to 6 carbon atoms; "n" represents an integer of 1 to 10; and "a" represents an integer of 0 to 2,

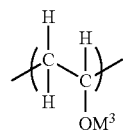

(3)

wherein $M^3$ represents a hydrogen atom, an acetyl group, or a siloxane group shown by the general formula (2).

Hereinafter, the present invention will be described in detail, but the present invention is not limited thereto.

Note that, in the present invention, tetrahydrofuran (THF) is used as a solvent in gel permeation chromatography (GPC) measurement.

<Cosmetic>

The inventive cosmetic contains an organosiloxane graft polyvinyl alcohol polymer described below.

[Organosiloxane Graft Polyvinyl Alcohol Polymer]

The organosiloxane graft polyvinyl alcohol polymer blended in the inventive cosmetic has a structural unit shown by the following general formula (1) and a structural unit shown by the following general formula (3). The organosiloxane graft polyvinyl alcohol polymer has a number average molecular weight (Mn) of 5,000 to 500,000 as measured by GPC in terms of polystyrene.

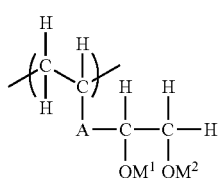
(1)

In the formula, $M^1$ and $M^2$ each represent a hydrogen atom, an acetyl group, or a siloxane group shown by the following general formula (2). At least one of $M^1$ and $M^2$ is a siloxane group shown by the following general formula (2). A represents a single bond or a linking group.

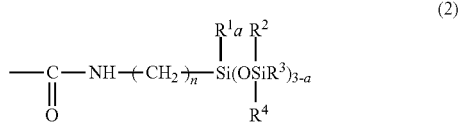
(2)

In the formula, $R^1$ represents a monovalent organic group having 1 to 6 carbon atoms. $R^2$, $R^3$, and $R^4$ each represent a monovalent organic group having 1 to 6 carbon atoms or a siloxy group shown by —$OSiR^5R^6R^7$, where $R^5$, $R^6$, and $R^7$ each represent a monovalent organic group having 1 to 6 carbon atoms. "n" represents an integer of 1 to 10, and "a" represents an integer of 0 to 2.

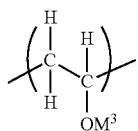
(3)

In the formula, $M^3$ represents a hydrogen atom, an acetyl group, or a siloxane group shown by the general formula (2).

Herein, $R^1$, $R^2$, $R^3$, $R^4$, $R^5$, $R^6$, and R, are each a monovalent organic group having 1 to 6 carbon atoms. Specifically, illustrative examples thereof include alkyl groups such as a methyl group, an ethyl group, a propyl group, and a butyl group; cycloalkyl groups such as a cyclopentyl group and a cyclohexyl group; aryl groups such as a phenyl group; alkenyl groups such as a vinyl group and an allyl group; substituted hydrocarbon groups such as a chloromethyl group and a 3,3,3-trifluoropropyl group; and the like. $R^1$, $R^2$, $R^3$, $R^4$, $R^5$, $R^6$, and $R^7$ may be the same or different from each other. In addition, $R^2$, $R^3$, and $R^4$ each may be a siloxy group shown by —$OSiR^5R^6R^7$. Illustrative examples of the siloxy group include a trimethylsiloxy group, an ethyldimethylsiloxy group, a phenyldimethylsiloxy group, a vinyldimethylsiloxy group, a chloromethyldimethylsiloxy group, a 3,3,3-trifluoropropyldimethylsiloxy group, and the like.

In the general formula (2), "a" represents an integer of 0 to 2. Preferably, in the general formula (2), "n" is 3, $R^2$, $R^3$, and $R^4$ are methyl groups, and "a" is 0.

In the general formula (1), A represents a single bond or a linking group. A is preferably a single bond. The organosiloxane graft polyvinyl alcohol polymer in which A is a single bond is more excellent in industrial productivity.

The inventive organosiloxane graft polyvinyl alcohol polymer is particularly preferably a reaction product of a (butenediol/vinyl alcohol) copolymer and tristrimethylsiloxysilylpropyl isocyanate. The modification rate of the tristrimethylsiloxysilylpropyl isocyanate is preferably 25 to 60%, further preferably 25 to 35%.

With respect to the molecular weight of the organosiloxane graft polyvinyl alcohol polymer blended in the inventive cosmetic, the number average molecular weight (Mn) may be within a range of 5,000 to 500,000, preferably 10,000 to 100,000, further preferably 20,000 to 50,000, as measured by GPC using tetrahydrofuran (THF) as a solvent in terms of polystyrene. When the number average molecular weight is less than 5,000, the film strength is low. Meanwhile, when the number average molecular weight is 500,000 or less, there is no fear of decreasing handleability and solubility.

The inventive organosiloxane graft polyvinyl alcohol polymer is blended in an amount of preferably 0.01 to 20 mass %, more preferably 0.1 to 10 mass %, relative to the total amount (mass) of the cosmetic.

(Method of Producing Organosiloxane Graft Polyvinyl Alcohol Polymer)

Next, a method of producing the organosiloxane graft polyvinyl alcohol polymer blended in the inventive cosmetic will be described. The organosiloxane graft polyvinyl alcohol polymer blended in the inventive cosmetic can be produced by reacting a polyvinyl alcohol resin compound having a structural unit shown by the following general formula (4) and a structural unit shown by the following formula (6) with an isocyanate group-containing organopolysiloxane shown by the following general formula (5),

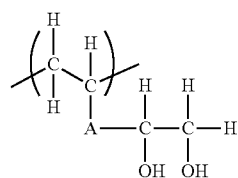
(4)

where A has the same meaning as above,

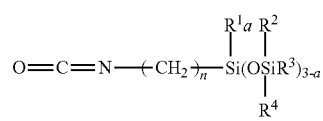
(5)

where $R^1$, $R^2$, $R^3$, $R^4$, "n", and "a" have the same meanings as above, and

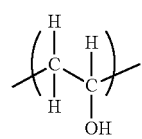
(6)

When the polyvinyl alcohol resin compound used as a raw material of the organosiloxane graft polyvinyl alcohol polymer has the structural unit shown by the general formula (4), the polyvinyl alcohol resin compound can easily dissolve in an organic solvent and can significantly improve the reaction rate with the isocyanate group-containing organopolysiloxane shown by the general formula (5). This allows the organosiloxane graft polyvinyl alcohol polymer to be effectively produced at industrially low cost.

According to such a method of producing the organosiloxane graft polyvinyl alcohol polymer, isocyanate groups having high reactivity can effectively react with hydroxyl groups of the polyvinyl alcohol resin compound. Thus, the organosiloxane graft polyvinyl alcohol polymer having the structural unit shown by the general formula (1) and the structural unit shown by the general formula (3) can be easily obtained.

As the isocyanate group-containing organopolysiloxane shown by the general formula (5), tristrimethylsiloxysilylpropyl isocyanate is preferably used.

When tristrimethylsiloxysilylpropyl isocyanate is used as the isocyanate group-containing organopolysiloxane shown by the general formula (5) as described above, the organosiloxane graft polyvinyl alcohol polymer with high modification rate can be effectively obtained.

The polyvinyl alcohol resin compound containing the structural unit shown by the general formula (4) and the structural unit shown by the formula (6) can be obtained, for example, by saponifying a polyvinyl acetate resin compound containing a structural unit shown by the following general formula (7) and a structural unit shown by the following formula (8),

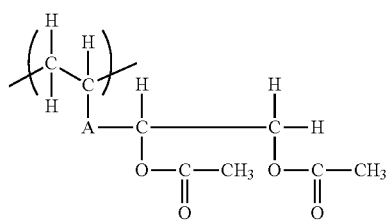

(7)

where A has the same meaning as above, and

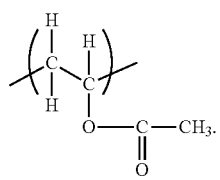

(8)

Although the polyvinyl alcohol resin compound used as a raw material of the organosiloxane graft polyvinyl alcohol polymer can be obtained by saponifying a polyvinyl acetate compound, the polyvinyl alcohol resin compound to be used may be a partially saponified compound.

In the case where a partially saponified polyvinyl alcohol resin compound is used to synthesize the organosiloxane graft polyvinyl alcohol polymer, an organosiloxane graft polyvinyl alcohol polymer containing the structural unit shown by the general formula (7) and the structural unit shown by the formula (8) can be obtained as a typical compound.

The polyvinyl acetate resin compound containing the structural unit shown by the general formula (7) and the structural unit shown by the formula (8) can be obtained by polymerizing a compound shown by the following general formula (9) and a compound shown by the following formula

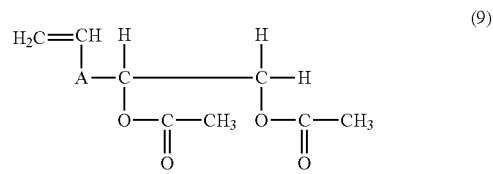

(9)

where A has the same meaning as above, and

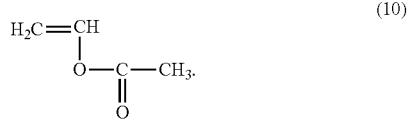

(10)

The molecular weight of the above-described polyvinyl alcohol resin compound can be appropriately selected such that the organosiloxane graft polyvinyl alcohol polymer has a molecular weight (i.e., a number average molecular weight (Mn) measured by GPC in terms of polystyrene) within a range of 5,000 to 500,000.

The polyvinyl alcohol resin compound may be a commercially product, G-Polymer™ available from Nippon Synthetic Chemical Industry Co., Ltd. Specifically, the compound may be selected from AZF8035W, OKS-6026, OKS-1011, OKS-8041, OKS-8049, OKS-1028, OKS-1027, OKS-1109, and OKS-1083.

The organosiloxane graft polyvinyl alcohol polymer can be produced by reacting hydroxyl groups of the polyvinyl alcohol resin compound with the isocyanate group-containing organopolysiloxane as described above. As the isocyanate group-containing organopolysiloxane, tristrimethylsiloxysilylpropyl isocyanate (i.e., a compound of the general formula (5) in which "n" is 3, $R^2$, $R^3$, and $R^4$ are methyl groups, and "a" is 0) is particularly preferably used. The reaction of the tristrimethylsiloxysilylpropyl isocyanate with the polyvinyl alcohol resin compound produces a tristrimethylsiloxysilylpropyl carbamate polyvinyl alcohol polymer having a structural unit shown by the following general formula (11),

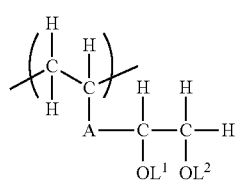

(11)

where $L^1$ and $L^2$ each represent a hydrogen atom, an acetyl group, or a siloxane group shown by the following formula (12), provided that at least one of $L^1$ and $L^2$ is a siloxane group shown by the following formula (12). A represents a single bond or a linking group.

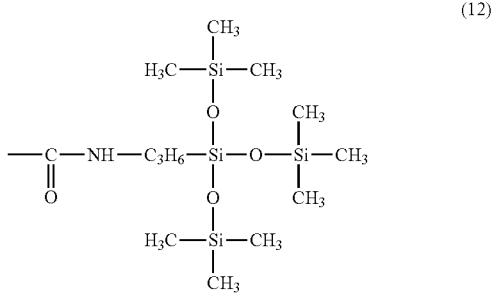

(12)

Moreover, although the organosiloxane graft polyvinyl alcohol polymer can be produced by the reaction between hydroxyl groups of the polyvinyl alcohol resin compound and the isocyanate group-containing organopolysiloxane as described above, this polyvinyl alcohol resin compound preferably contains a polybutenediol structure (i.e., a structure of the general formula (4) in which A is a single bond). Incorporating the polybutenediol structure makes it possible to effectively obtain an organosiloxane graft polyvinyl alcohol polymer having high solubility into an organic solvent and high modification rate. This polymer has a structural unit shown by the following general formula (13),

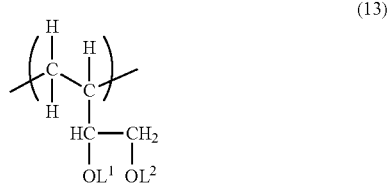

(13)

where $L^1$ and $L^2$ have the same meanings as above.

Since the above-described method of producing the organosiloxane graft polyvinyl alcohol polymer employs the urethane bond formation reaction of hydroxyl groups of the polyvinyl alcohol resin compound with the isocyanate group-containing organopolysiloxane, a specific reaction condition and a specific reaction apparatus are not required. However, a solvent is preferably used to mix the polyvinyl alcohol resin compound with the isocyanate group-containing organopolysiloxane and perform the reaction efficiently and controllably. Examples of the solvent include esters such as methyl acetate, ethyl acetate, and butyl acetate; ketones such as acetone, methyl ethyl ketone, and cyclohexanone; aromatic hydrocarbons such as toluene and xylene; ethers such as diethyl ether and tetrahydrofuran; amides such as N,N-dimethylformamide and N-methylpyrrolidone; and sulfoxides such as dimethylsulfoxide. These may be used solely or in mixture of two or more kinds.

Moreover, the reaction is generally performed at 20 to 150° C. for 1 to 24 hours although the conditions depend on the kind of the solvent used in the reaction. In this case, a known catalyst used for forming urethane bond may be added. The catalyst includes amines such as triethylamine, triethylenediamine, and N-methylmorpholine; and organometallic compounds such as di-n-butyl tin dilaurate and stannous oleate. After completion of the reaction, washing and drying may be performed to obtain the intended organosiloxane graft polyvinyl alcohol polymer.

[Other Components]

The inventive cosmetic may be blended with various other components used in usual cosmetics. Examples of the other components include (1) an oil agent, (2) a powder, (3) a surfactant, (4) a crosslinked organopolysiloxane, (5) a film former, (6) an aqueous component, (7) a wax, and (8) other additive. These can be used solely or in an appropriate combination of two or more kinds. These components are appropriately selected for use depending on the kind of the cosmetic, and so on. The amount of these components to be blended can be a known amount which depends on the kind of the cosmetic, and so on.

(1) Oil Agent

The oil agent may be in any form of solid, semi-solid, or liquid at room temperature. Examples thereof include silicone oils, natural animal and vegetable fats and oils, semi-synthetic fats and oils, hydrocarbon oils, higher alcohols, fatty acids, ester oils, fluorinated oil agents, and the like. In the case where an oil agent is blended, the amount of the oil agent blended is not particularly limited, but is preferably 1 to 85 mass %, more preferably 15 to 40 mass %, relative to the total amount of the cosmetic.

Silicone Oil

The silicone oil is not particularly limited as long as the raw material can be blended in usual cosmetics. Specifically, the silicone oil includes low viscous to high viscous linear or branched organopolysiloxanes such as dimethyl polysiloxane, decamethyl cyclopentasiloxane, dodecamethyl cyclohexasiloxane, disiloxane, trisiloxane, methyl trimethicone, caprylyl methicone, methylphenylpolysiloxane, methylhexylpolysiloxane, methyl hydrogen polysiloxane, and dimethylsiloxane/methylphenylsiloxane copolymers; silicone rubbers such as amino-modified organopolysiloxanes, pyrrolidone-modified organopolysiloxanes, pyrrolidone carboxylate-modified organopolysiloxanes, gum dimethyl polysiloxanes with high polymerization degree, gum amino-modified organopolysiloxanes, and gum dimethylsiloxane/methylphenylsiloxane copolymers; silicone gum and rubber cyclic organopolysiloxane solutions, trimethylsiloxysilicate, trimethylsiloxysilicate cyclic siloxane solutions and higher alkoxy-modified silicones such as stearoxysilicone; higher fatty acid-modified silicones, alkyl-modified silicones, long chain alkyl-modified silicones, amino acid-modified silicones, fluorine-modified silicones, silicone resins, melts of silicone resins, and the like. Among these, it is particularly preferable to utilize: volatile silicones and low viscous silicones which provide refreshing feeling on use [commercially available products such as TMF-1.5, KF-995, KF-96A-2cs, and KF-96A-6cs manufactured by Shin-Etsu Chemical Co., Ltd.], phenyl silicones used to improve the compatibility with oil agents and to impart glossiness [commercially available products such as KF-56A and 54HV manufactured by Shin-Etsu Chemical Co., Ltd.], and silicone waxes used to impart glossiness and adjust feeling on use [commercially available products such as KP-561P, 562P, and KF-7020S manufactured by Shin-Etsu Chemical Co., Ltd.]. Particularly, phenyl silicones have gel formation ability with the organosiloxane graft polyvinyl alcohol polymer blended in the inventive cosmetic, and thereby exhibit excellent performances as a thickener, a stabilizer, and a touch-sensation improver, so that the phenyl silicones can be used to improve the adhesion of lipstick, lip gloss, and the like. These silicone oils carl be used alone or in combination of two or more kinds.

(2) Powder

The powder is not particularly limited as long as the raw material can be blended in usual cosmetics. Examples thereof include pigments, silicone powders, and the like. In the case where a powder is blended, the amount of the powder blended is not particularly limited, but is desirably 0.1 to 90 mass %, further preferably 1 to 35 mass %, relative to the total amount of the cosmetic.

Pigments

The pigments are not particularly limited as long as the pigment is used in normal make-up cosmetics. Examples thereof include inorganic pigments such as talc, mica, kaolin, silica, calcium carbonate, zinc oxide, titanium oxide, red iron oxide, yellow iron oxide, black iron oxide, ultramarine blue, Prussian blue, carbon black, titanium suboxide, cobalt violet, chromium oxide, chromium hydroxide, cobalt titanate, bismuth oxychloride, and titanium-mica pearl pigments; organic pigments such as zirconium, barium or aluminum lake of Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404, and Green No. 3 and the like; natural dyes such as chlorophyll and β-carotene; dyes; and the like. In addition, a pigment hydrophobized with silicone or the like can also be used. Specific examples of the hydrophobized inorganic powders include dispersions containing hydrophobized fine-particle titanium oxide or hydrophobized fine-particle zinc oxide which are commercially available under product names such as SPD-T5, T6, T5L, Z5, Z6, and Z5L (all of which are manufactured by Shin-Etsu Chemical Co., Ltd.).

Silicone Powders

The silicone powders include crosslinked silicone powders (i.e., what is called silicone rubber powders of organopolysiloxanes having such a structure that repeating chains of diorganosiloxane units are crosslinked), silicone resin particles (polyorganosilsesquioxane resin particles having a three-dimensional network structure), and the like. As specific examples thereof, names such as (dimethicone/vinyl dimethicone) crosspolymer and polymethylsilsesquioxane are known. These are commercially available as powder or swollen material containing silicone oil under product names such as, for example, KMP-598, 590, 591, and KSG-016F (all of which are manufactured by Shin-Etsu Chemical Co., Ltd.). These powders can be used alone or in combination of two or more kinds.

Particularly, silicone resin-coated silicone rubber powders are used in sunscreen, make-up, concealer, and the like because of the effect of improving the tactile feel, for example, preventing stickiness, the effect of correcting the shapes on wrinkles, pores, and the like, and other effects. As specific examples of the silicone resin-coated silicone rubber powders, names such as (vinyl dimethicone/methicone silsesquioxane) crosspolymer, (diphenyl dimethicone/vinyldiphenyl dimethicone/silsesquioxane) crosspolymer, polysilicone-22, and polysilicone-1 crosspolymers are known, which are defined in a Japanese Labeling Name of Cosmetic Ingredient. These are commercially available under product names such as KSP-100, 101, 102, 105, 300, 411, and 441 (all of which are manufactured by Shin-Etsu Chemical Co., Ltd.). These powders can be used alone or In combination of two or more kinds.

(3) Surfactant

The surfactant includes nonionic, anionic, cationic and amphoteric surfactants, but is not particularly limited, and any of these can be used as long as it is used in usual cosmetics. One kind of the surfactant can be used solely, or two or more kinds thereof can be used in an appropriate combination. Among these surfactants, preferable are partially crosslinked polyether-modified silicones, partially crosslinked polyglycerin-modified silicones, linear or branched polyoxyethylene-modified organopolysiloxanes, linear or branched polyoxyethylene-polyoxypropylene-modified organopolysiloxanes, linear or branched polyoxyethylene/alkyl-co-modified organopolysiloxanes, linear or branched polyoxyethylene-polyoxypropylene/alkyl-co-modi fied organopolysii oxanes, linear or branched polyglycerin-modified organopolysiloxanes, and linear or branched polyglycerin/alkyl-co-modified organopolysiloxanes. In these surfactants, the content of hydrophilic polyoxyethylene groups, polyoxyethylene-polyoxypropylene groups, or polyglycerin residues is preferably 10 to 70 mass % in the molecule. Specific examples of the surfactant include KSG-210, 240, 310, 320, 330, 340, 320Z, 350Z, 710, 810, 820, 830, 840, 820Z, 850Z, KF-6011, 6013, 6043, 6028, 6038, 6048, 6100, 6104, 6105, and 6106, which are manufactured by Shin-Etsu Chemical Co., Ltd, and the like. In the case where this component is blended, the blended amount is preferably 0.01 to 15 mass % in the cosmetic.

(4) Crosslinked Organopolysiloxane

The crosslinked organopolysiloxane is not particularly limited as long as it is used in usual cosmetic products. One kind of the crosslinked organopolysiloxane can be used solely, or two or more kinds thereof can be used in an appropriate combination. Unlike the silicone powders and the surfactants respectively described in (2) and (3) above, the crosslinked organopolysiloxane is a compound having no polyether- or polyglycerin structure in the molecular structure, but is an elastomer having structural viscosity by swelling with the oil agent. Examples of the crosslinked organopolysiloxane include (dimethicone/vinyl dimethicone) crosspolymers, (dimethicone/phenylvinyl dimethicone) crosspolymers, (vinyl dimethicone/lauryl dimethicone) crosspolymers, (lauryl polydimethylsiloxyethyl dimethicone/bis-vinyl dimethicone) crosspolymers, and the like. These are commercially available as swollen materials containing oil which is liquid at room temperature. Specific examples thereof include KSG-15, 1510, 16, 1610, 18A, 19, 41A, 42A, 43, 44, 042Z, 045Z, and 048Z, which are manufactured by Shin-Etsu Chemical Co., Ltd., and the like. In the case where this component is blended, the blended amount is preferably 0.01 to 30 mass % in the cosmetic.

(5) Film Former

The film former is not particularly limited as long as the raw material can be blended in usual cosmetics. Specifically, used as the film former are: latexes such as polyvinyl alcohol, polyvinylpyrrolidone, polyvinyl acetate, and polyalkyl acrylate; cellulose derivatives such as dextrin, alkyl cellulose and nitrocellulose; siliconized polysaccharides such as pullulan tris(trimethylsiloxy)silylpropylcarbamate; acrylic-silicone graft copolymers such as (alkyl acrylate/dimethicone) copolymers; silicone resins such as trimethylsiloxysilicate; silicone-based resins such as silicone-modified polynorbornene and fluorine-modified silicone resins; fluorinated resins, aromatic hydrocarbon resins, polymer emulsion resins, terpene-based resins, polybutene, polyisoprene, alkyd resins, polyvinylpyrrolidone-modified polymers, rosin-modified resins, polyurethanes, and the like.

Among these, silicone-based film formers are particularly preferable. Above all, it is possible to use, without limitation to, pullulan tris(trimethylsiloxy)silylpropyl carbamate [commercially available products, dissolved in a solvent, include TSPL-30-D5 and ID manufactured by Shin-Etsu Chemical Co., Ltd.], (alkyl acrylate/dimethicone) copolymers [commercially available products, dissolved in a solvent, include KP-543, 545, 549, 550, and 545L manufactured by Shin-Etsu Chemical Co., Ltd., and the like], trimethylsiloxysilicate [commercially available products, dissolved in a solvent, include KF-7312J and X-21-5250 manufactured by Shin-Etsu Chemical Co., Ltd., and the like], and silicone-modified polynorbornene [commercially available products, dissolved in a solvent, include NBN-30-ID manufactured by Shin-Etsu Chemical Co., Ltd., and the like]. The film formers can be used alone or in combination of two or more kinds. In the case where this component is blended, the blended amount is preferably 0.1 to 20 mass % in the cosmetic.

(6) Aqueous Component

The aqueous component is not particularly limited as long as the aqueous component can be blended in usual cosmetics. Specifically, the aqueous component includes water, moisturizers, and the like. These can be used solely or in an appropriate combination of two or more kinds. In the case where this component is blended, the blended amount is preferably 0.1 to 90 mass % in the cosmetic.

Water

The water includes purified water generally used in cosmetics as well as sea water, hot spring water, peat water, distilled water from fruits and plants, and the like.

Moisturizers

The moisturizers include lower alcohols such as ethanol and isopropanol; sugar alcohols such as sorbitol, maltose, and xylitol; polyvalent alcohols such as butylene glycol, dibutylene glycol, propylene glycol, dibutylene glycol, pentylene glycol, decanediol, octanediol, hexanediol, erythritol, glycerin, diglycerin, and polyethylene glycol; glucose, glyceryl glucoside, betaine, hyaluronic acid, chondroitin sulfate, pyrrolidone carboxylate, polyoxyethylene methyl glucoside, polyoxypropylene methyl glucoside, and the like.

(7) Wax

The wax used in the present invention is not particularly limited as long as the raw material can be blended in usual cosmetics. Specifically, the wax include hydrocarbon waxes such as ceresin, ozokerite, paraffin, synthetic wax, microcrystalline wax, and polyethylene wax; plant-derived waxes such as carnauba wax, rice wax, rice bran wax, jojoba wax (including extremely hydrogenated jojoba oil), and candelilla wax; animal-derived waxes such as whale wax, beeswax, and Chinese wax; and the like. These waxes can be used alone or in combination of two or more kinds. In the case where a wax is blended, the blended amount is preferably 0.1 to 10 mass % in the cosmetic.

(8) Other Additives

The other additives include an oil-soluble gelling agent, antiperspirant, ultraviolet absorber, preservative and antimicrobial, fragrance, salt, antioxidant, pH adjuster, chelating agent, cooling agent, anti-inflammatory agent, skincare component (such as whitening agent, cell activator, rough skin improver, blood circulation promoter, skin astringent, antiseborrheic agent), vitamin, amino acid, water-soluble polymer compound, fiber, inclusion compound, and the like.

Oil-Soluble Gelling Agent

The oil-soluble gelling agent includes metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate, dextrin stearate, and dextrin 2-ethylhexanoate/palmitate; sucrose fatty acid esters such as sucrose palmitate and sucrose stearate; fructo-oligosaccharide fatty acid esters such as fructo-oligosaccharide stearate and fructo-oligosaccharide 2-ethylhexanoate; benzylidene derivatives of sorbitol such as monobenzylidene sorbitol and dibenzylidene sorbitol; organic-modified clay minerals of disteardimonium hectorite, stearalkonium hectorite, and hectorite; and the like.

Ultraviolet Absorber

The ultraviolet absorber includes homomenthyl salicylate, octocrylene, 4-tert-butyl-4'-methoxydibenzoyl methane, 4-(2-β-glucopyranosiloxy)propoxy-2-hydroxybenzophenone, octyl salicylate, hexyl 2-[4-(diethylamino)-2-hydroxybenzoyl]benzoate, dihydroxydimethoxybenzophenone, sodium dihydroxydimethoxybenzophenone disulfonate, dihydroxybenzophenone, dimethicodiethylbenzal malonate, 1-(3,4-dimethoxyphenyl)-4,4-dimethyl-1,3-pentanedione, 2-ethylhexyl dimethoxybenzylidene dioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methylbis(trimethylsiloxy)silylisopentyl trimethoxycinnamate, drometrizole trisiloxane, 2-ethylhexyl p-dimethylaminobenzoate, isopropyl p-methoxycinnamate, 2-ethylhexyl p-methoxycinnamate, 2,4-bis-[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenonesulfonic acid and trihydrates thereof, sodium hydroxymethoxybenzophenonesulfonate, phenylbenzimidazolesulfonic acid, and 2,2'-methylenebis(6-(2H-benzotriazol-2-yl)-4-(1,1,3,3-tetramethylbutyl)phenol. Moreover, it is possible to use a combination of UVA absorbers (such as, for example, diethylamino hydroxybenzoyl hexyl benzoate) and UVB absorbers (such as, for example, ethylhexyl methoxycinnamate), each of which can also be used in any combination.

Preservative and Antimicrobial

The preservative and antimicrobial include alkyl paraoxybenzoate, benzoic acid, sodium benzoate, sorbic acid, potassium sorbate, phenoxy ethanol, imidazolidinyl urea, salicylic acid, isopropylmethylphenol, phenol, p-chloro-m-cresol, hexachlorophene, benzalkonium chloride, chlorhexidine chloride, trichlorocarbanilide, iodopropynyl butylcarbamate, polylysine, photosensitizers, silver, plant extracts, and the like.

The state of the above-described cosmetic may be either emulsion or nonaqueous. When fresh feeling on use is to be imparted, an emulsion state is selected. The emulsion state may be any of O/W type emulsion and W/O type emulsion. When oiliness or water resistance is desired, a nonaqueous composition can be selected. In both cases, favorable cosmetic is obtained. Note that, in the present invention, "nonaqueous composition" refers to a composition containing substantially no water.

The cosmetic per se of the present invention is not particularly limited as long as the cosmetic contains the essential component. For example, the present invention is applicable to various products such as beauty essence, milky lotion, cream, hair care product, foundation, makeup base, sunscreen, concealer, cheek color, lipstick, gloss, balm, mascara, eye shadow, eyeliner, body make-up, deodorant, and manicure product. The physical form of the inventive cosmetic can be selected from various physical forms such as liquid, cream, solid, paste, gel, mousse, souffle, clay, powder, and stick forms.

EXAMPLES

Hereinafter, the present invention will be further described by way of Examples and Comparative Examples, but the present invention is not limited thereto. Unless otherwise particularly stated, the amounts of ingredients are indicated in percent by mass.

[Production Example 1] Production of tris(trimethylsiloxy)silylpropyl carbamate (butenediol/vinyl alcohol) copolymer (polymer (I))

A flask equipped with a dropping funnel, a cooling pipe, a thermometer, and a stirrer was charged with 20 g of G-Polymer (OKS-1011; polymerization degree: 300, saponification rate: 98.5%) available from Nippon Synthetic Chemical Industry Co., Ltd., as the polyvinyl alcohol resin compound containing the structural unit shown by the general formula (4) and the structural unit shown by the formula (6), 180 g of N-methylpyrrolidone, 0.6 g of triethylamine, and 52.5 g of tristrimethylsiloxysilylpropyl isocyanate, so that the reaction was performed at 90° C. for 4 hours. After completion of the reaction, a reaction product was precipitated in a mixed solution of water and methanol, and further repeatedly washed with a mixed solution of water and methanol. The product was then dried under reduced pressure at 70° C. for 24 hours to obtain 58.0 g of a polymer. FIG. 1 shows an IR analysis result of the polymer. The IR analysis result showed that the absorption of isocyanate groups at 2,270 cm$^{-1}$ almost disappeared and identified the obtained polymer as a tris(trimethylsiloxy)silylpropyl carbamate (butenediol/vinyl alcohol) copolymer having the structural unit shown by the general formula (1) and the structural unit shown by the general formula (3). The number average molecular weight (Mn) measured by GPC using THF as a solvent was 26,000 in terms of polystyrene, and the molecular weight distribution was 1.61. The modification rate of the obtained polymer was 29.4 mol %.

[Production Example 2] Production of tris(trimethylsiloxy)silylpropyl carbamate (butenediol/vinyl alcohol) copolymer (polymer (II))

The same apparatus as in Production Example 1 was used and charged with 20 g of G-Polymer (OKS-1083; polymerization degree: 1,900, saponification rate: 99.8%) available from Nippon Synthetic Chemical Industry Co., Ltd., as the polyvinyl alcohol resin compound containing the structural unit shown by the general formula (4) and the structural unit shown by the formula (6), 180 g of N-methylpyrrolidone, 0.6 g of triethylamine, and 52.5 g of tristrimethylsiloxysilylpropyl isocyanate, so that the reaction was performed at 90° C. for 4 hours. After completion of the reaction, a reaction product was precipitated in a mixed solution of water and methanol, and further repeatedly washed with a mixed solution of water and methanol. The product was then dried under reduced pressure at 70° C. for 24 hours to obtain 65.5 g of a polymer. The IR analysis result showed that the absorption of isocyanate groups at 2,270 cm$^{-1}$ almost disappeared and identified the obtained polymer as a tris(trimethylsiloxy) silylpropyl carbamate (butenediol/vinyl alcohol) copolymer having the structural unit shown by the general formula (1) and the structural unit shown by the general formula (3). The number average molecular weight (Mn) measured by GPC using THF as a solvent was 68,000 in terms of polystyrene, and the molecular weight distribution was 1.23. The modification rate of the obtained polymer was 29.0 mol %.

[Production Example 3] Preparation of Polymer (I) Solution (30 Mass %) in Isododecane The polymer (I) and isododecane were put into a separable flask purged with nitrogen. After uniform dissolution at 80° C. using a glass stirrer, a 30 mass % solution was prepared.

[Production Example 4] Preparation of Polymer (I) Solution (20 Mass %) in Decamethylcyclopentasiloxane (D5)

The polymer (I) and D5 were put into a separable flask purged with nitrogen. After uniform dissolution at 80° C. using a glass stirrer, a 20 mass % solution was prepared.

[Production Example 5] Preparation of Polymer (II) Solution (20 Mass %) in Isododecane The polymer (II) and isododecane were put into a separable flask purged with nitrogen. After uniform dissolution at 80° C. using a glass stirrer, a 20 mass % solution was prepared.

[Production Example 6] Preparation of Polymer (II) Solution (20 Mass %) in D5

The polymer (II) and D5 were put into a separable flask purged with nitrogen. After uniform dissolution at 80° C. using a glass stirrer, a 20 mass % solution was prepared.

Incidentally, the obtained polymers can be dissolved not only in isododecane and D5 but also in volatile solvents used in cosmetic products, such as dimethicone (2cs) and methyl trimethicone, as well as nonvolatile solvents such as triethylhexanoin and isotridecyl isononanoate. Moreover, the viscosity of these solutions can be changed depending on the composition and molecular weight of the polymers.

While dissolved in a volatile polymer, the polymer blended in the inventive cosmetic forms a tough and soft film as described above. Thus, the obtained polymers even in a small amount are expected to improve the oil resistance of the cosmetic.

<Characteristic Evaluation>

Cosmetics of Examples 1 to 3 and Comparative Examples 1 to 11 described later were evaluated in terms of cosmetic feeling on use (non-stickiness), spreadability (flexibility), finish (transparency) and cosmetic durability (oil resistance, persistency: evaluated after 8 hours from the application) according to evaluation criteria shown in Table 1. The obtained evaluation results were assessed according to the following assessment criteria based on average values of 10 panelists. These results are also shown in Tables 2, 3, and 4.

<Evaluation Criteria>

TABLE 1

| Item | Feeling on use | Spreadability | Finish | Cosmetic durability |
|---|---|---|---|---|
| 5 points | good | good | good | good |
| 4 points | fair | fair | fair | fair |
| 3 points | normal | normal | normal | normal |
| 2 points | somewhat bad | somewhat bad | somewhat bad | somewhat bad |
| 1 point | bad | bad | bad | bad |

<Assessment Criteria>
I: the average point is 4.5 points or more
II: the average point is 3.5 points or more but less than 4.5 points
III: the average point is 2.5 points or more but less than 3.5 points
IV: the average point is 1.5 points or more but less than 2.5 points
V: the average point is less than 1.5 points

TABLE 2

| | Ingredients | Example 1 | Comparative Example 1 | 2 | 3 | 4 | 5 |
|---|---|---|---|---|---|---|---|
| (1) | Polymer (I) solution in D5 (20 mass %) | 3 | | | | | |
| | Trimethylsiloxysilcate solution in D5 (Note 1) (50 mass %) | | | 1.2 | 0.6 | 0.6 | |
| | Highly polymerized dimethyl polysiloxane solution in D5 (Note 2) (20 mass %) | | | | 1.5 | | |
| | Acrylic-silicone graft copolymer solution in D5 (Note 3) (30 mass %) | | | | | 1 | 2 |
| | Decamethyl-cyclopentasiloxane | | 3 | 1.8 | 0.9 | 0.9 | 1 |
| (2) | Partially crosslinked polyether-modified silicone composition (Note 4) | 3.5 | 3.5 | 3.5 | 3.5 | 3.5 | 3.5 |
| | Partially crosslinked dimethyl polysiloxane composition (Note 5) | 5 | 5 | 5 | 5 | 5 | 5 |
| | Silicone-branched polyether-modified silicone (Note 6) | 2 | 2 | 2 | 2 | 2 | 2 |
| | Organic-modified clay mineral | 1.2 | 1.2 | 1.2 | 1.2 | 1.2 | 1.2 |
| | Dimethyl polysiloxane (6 cs) | 6.5 | 6.5 | 6.5 | 6.5 | 6.5 | 6.5 |
| | Decamethyl-cyclopentasiloxane | 18.6 | 18.6 | 18.6 | 18.6 | 18.6 | 18.6 |
| (3) | Triethylhexanoin | 5 | 5 | 5 | 5 | 5 | 5 |
| | Silicone-branched polyglycerin-modified silicone (Note 7) | 0.2 | 0.2 | 0.2 | 0.2 | 0.2 | 0.2 |
| | Silicone-treated titanium oxide (Note 8) | 8.5 | 8.5 | 8.5 | 8.5 | 8.5 | 8.5 |
| | Silicone-treated yellow iron oxide (Note 8) | 0.75 | 0.75 | 0.75 | 0.75 | 0.75 | 0.75 |
| | Silicone-treated red iron oxide (Note 8) | 0.14 | 0.14 | 0.14 | 0.14 | 0.14 | 0.14 |
| | Silicone-treated black iron oxide (Note 8) | 0.01 | 0.01 | 0.01 | 0.01 | 0.01 | 0.01 |
| (4) | Dipropylene glycol | 5 | 5 | 5 | 5 | 5 | 5 |
| | Preservative | q.s. | q.s. | q.s. | q.s. | q.s. | q.s. |
| | Purified water | balance | balance | balance | balance | balance | balance |
| | Total | 100 | 100 | 100 | 100 | 100 | 100 |
| | Evaluation results | | | | | | |
| | Feeling on use | I | I | II | III | I | I |
| | Spreadability | I | I | II | II | I | I |
| | Finish | I | I | IV | III | III | II |
| | Cosmetic durability | I | V | IV | IV | IV | IV |

(Note 1)
Trimethylsiloxysilicate solution; KF-7312J (manufactured by Shin-Etsu Chemical Co., Ltd.)
(Note 2)
Highly polymerized dimethyl polysiloxane solution; KF-9028 (manufactured by Shin-Etsu Chemical Co., Ltd.)
(Note 3)
Acrylic-silicone graft copolymer solution; KP-545 (manufactured by Shin-Etsu Chemical Co., Ltd.)
(Note 4)
Partially crosslinked polyether-modified silicone composition; KSG-210 <crosslinked portion: 2 to 30%, dimethicone (6 cs): 70 to 80%> (manufactured by Shin-Etsu Chemical Co., Ltd.)
(Note 5)
Partially crosslinked dimethyl polysiloxane composition; KSG-15 <crosslinked portion: 4 to 10%, decamethylcyclopentasiloxane: 90 to 96%> (manufactured by Shin-Etsu Chemical Co., Ltd.)
(Note 6)
Silicone-branched polyether-modified silicone; KF-6028 (manufactured by Shin-Etsu Chemical Co., Ltd.)

(Note 7)
Silicone-branched polyglycerin-modified silicone; KF-6106 (manufactured by Shin-Etsu Chemical Co., Ltd.)
(Note 8)
Silicone-treated powder; silicone-treated powder whose particle surfaces were hydrophobized with KF-9909 (manufactured by Shin-Etsu Chemical Co., Ltd.)

<Preparation of Cosmetic>
A: The ingredients in (3) were prepared into a paste with a three-roll mill, and uniformly mixed with the ingredients in (2).
B: The ingredients in (4) were uniformly mixed.
C: The mixture B was added to the mixture A and emulsified, and the ingredients in (1) were added thereto. Thus, a foundation was obtained.

The results in Table 2 revealed that the inventive cosmetic, that is, the foundation of Example 1 has favorable feeling on use (non-stickiness), spreadability (flexibility), finish (transparency) and cosmetic durability (oil resistance, persistency: evaluated after 8 hours from the application) in comparison with Comparative Examples 1 to 5.

Example 2, Comparative Examples 6 to 10

Mascaras were prepared according to formulations shown in Table 3. The obtained mascaras were subjected to the characteristic evaluation of spreadability, finish, and cosmetic durability. Table 3 also shows the evaluation results.

TABLE 3

| | | Example | Comparative Example | | | | |
|---|---|---|---|---|---|---|---|
| | Ingredients | 2 | 6 | 7 | 8 | 9 | 10 |
| (1) | Polymer (I) solution in isododecane (30 mass %) | 20 | | | | | |
| | Trimethylsiloxysilicate solution in isododecane (Note 1) (60 mass %) | | | 10 | 5 | 5 | |
| | Highly polymerized dimethyl polysiloxane (1 million cs) | | | | 3 | | |
| | Acrylic-silicone graft copolymer solution in isododecane (Note 2) (40 mass %) | | | | | 7.5 | 15 |
| (2) | Dextrin palmitate (Note 3) | 2 | 2 | 2 | 2 | 2 | 2 |
| | Ceresin | 7 | 7 | 7 | 7 | 7 | 7 |
| | Microcrystalline wax | 7 | 7 | 7 | 7 | 7 | 7 |
| | Isododecane | 30 | 30 | 30 | 30 | 30 | 30 |
| (3) | Organic-modified clay mineral | 5 | 5 | 5 | 5 | 5 | 5 |
| | Silicone-treated black iron oxide (Note 4) | 5 | 5 | 5 | 5 | 5 | 5 |
| | Silicone-treated talc (Note 4) | 5 | 5 | 5 | 5 | 5 | 5 |
| | Polymethylsilsesquioxane (Note 5) | 5 | 5 | 5 | 5 | 5 | 5 |
| | Silicone-branched polyether-modified silicone (Note 6) | 1.2 | 1.2 | 1.2 | 1.2 | 1.2 | 1.2 |
| | Propylene carbonate | 1.6 | 1.6 | 1.6 | 1.6 | 1.6 | 1.6 |
| | Preservative | q.s. | q.s. | q.s. | q.s. | q.s. | q.s. |
| | Isododecane | balance | balance | balance | balance | balance | balance |
| | Total | 100 | 100 | 100 | 100 | 100 | 100 |
| | Evaluation results | | | | | | |
| | Spreadability | I | I | I | II | II | II |
| | Finish | I | I | IV | IV | II | I |
| | Cosmetic Durability | I | V | IV | IV | IV | IV |

(Note 1)
Trimethylsiloxysilicate solution; X-21-5595 (manufactured by Shin-Etsu Chemical Co., Ltd.)
(Note 2)
Acrylic-silicone graft copolymer solution; KP-550 (manufactured by Shin-Etsu Chemical Co., Ltd.)
(Note 3)
Dextrin palmitate; Rheopearl KL2 (manufactured by Chiba Flour Milling Co., Ltd.)
(Note 4)
Silicone-treated powder; silicone-treated powder whose particle surfaces were hydrophobized with KF-9909 (manufactured by Shin-Etsu Chemical Co., Ltd.)

TABLE 3-continued

|  | Example | Comparative Example | | | | |
|---|---|---|---|---|---|---|
| Ingredients | 2 | 6 | 7 | 8 | 9 | 10 |

(Note 5)
Polymethylsilsesquioxane; KMP-590 (manufactured by Shin-Etsu Chemical Co., Ltd.)
(Note 6)
Silicone-branched polyether-modified silicone; KF-602.8 (manufactured by Shin-Etsu Chemical Co., Ltd.)

<Preparation of Cosmetic>
A: The ingredients in (2) were dissolved by heating at 85° C. and then uniformly mixed.
B: The ingredients in (1) and (3) were added to the mixture A, and uniformly mixed at 80° C.
C: The mixture B was gradually cooled. Thus, a mascara was obtained.

The results in Table 3 revealed that the inventive cosmetic, that is, the mascara of Example 2 has favorable spreadability (flexibility), finish (transparency) and cosmetic durability (oil resistance, persistency: evaluated after 8 hours from the application) in comparison with Comparative Examples 6 to 10. Moreover, it was revealed that the inventive cosmetic is favorable regardless of emulsion or nonaqueous.

Example 3, Comparative Example 11

Sunscreen creams were prepared according to formulations shown in Table 4. The obtained sunscreen creams were subjected to the characteristic evaluation of feeling on use and cosmetic durability as well as water-resistance SPF test. Table 4 also shows the evaluation results. The water-resistance SPF test was conducted according to the FDA method. Note that when no film former in the ingredients in (1) was blended, the SPF value was 15 as measured by Japan Cosmetic Industry Association Standard SPF Test Method (ISO24444).

TABLE 4

| | Ingredients | Example 3 | Comparative Example 11 |
|---|---|---|---|
| (1) | Polymer (I) solution in D5 (20 mass %) | 5 | |
| | Acrylic-silicone graft copolymer solution in D5 (Note 1) (30 mass %) | | 5 |
| (2) | Partially crosslinked polyether-modified silicone composition (Note 2) | 3 | 3 |
| | Phenyl modified partially crosslinked dimethyl polysiloxane composition (Note 3) | 3 | 3 |
| | Alkyl/silicone-branched polyether-modified silicone (Note 4) | 2 | 2 |
| | Decamethylcyclopentasiloxane | 0.5 | 0.5 |
| | Diphenylsiloxy phenyl trimetnicone (Note 5) | 5 | 5 |
| | 2-Ethylhexyl p-methoxycinnamate | 7.5 | 7.5 |
| (3) | 1,3-Butylene glycol | 5.5 | 5.5 |
| | Sodium citrate | 0.2 | 0.2 |
| | Sodium chloride | 0.5 | 0.5 |
| | Preservative | q.s. | q.s. |
| | Purified water | balance | balance |
| Total | | 100 | 100 |

TABLE 4-continued

| Ingredients | Example 3 | Comparative Example 11 |
|---|---|---|
| Evaluation results | | |
| Feeling on use | I | I |
| Cosmetic durability | I | III |
| Water-resistance SPF | 15 | 16 |

(Note 1)
Acrylic-silicone graft copolymer solution; KP-545 (manufactured by Shin-Etsu Chemical Co., Ltd.)
(Note 2)
Partially crosslinked polyether-modified silicone composition; KSG-210 <crosslinked portion: 2 to 30%, dimethyl polysiloxane (6 cs): 70 to 80%> (manufactured by Shin-Etsu Chemical Co., Ltd.)
(Note 3)
Phenyl-modified partially crosslinked dimethyl polysiloxane composition; KSG-18A <crosslinked portion: 10 to 20%, diphenylsiloxy phenyl trimethicone: 80 to 90%> (manufactured by Shin-Etsu Chemical Co., Ltd.)
(Note 4)
Alkyl/silicone-branched polyether-modified silicone; KF-6038 (manufactured by Shin-Etsu Chemical Co., Ltd.))
(Note 5)
Diphenylsiloxy phenyl trimethicone; KF-56A (manufactured by Shin-Etsu Chemical Co., Ltd.)

<Preparation of Cosmetic>
A: The ingredients in (2) were uniformly mixed.
B: The ingredients in (3) were uniformly mixed.
C: The mixture B was added to the mixture A and emulsified, and the ingredients in (1) were added thereto. Thus, a sunscreen cream was obtained.

The results in Table 4 revealed that the inventive cosmetic, that is, the sunscreen cream of Example 3 has favorable cosmetic durability (oil resistance, persistency: evaluated after 8 hours from the application) and improved oil resistance in comparison with Comparative Example 11, and also has water resistance comparable to that of the conventional film former.

[Example 4] W/O sunscreen milk

| | (Ingredients) | Mass (%) |
|---|---|---|
| 1. | Polymer (I) solution in D5 (20 mass %) | 3 |
| 2. | Phenyl-modified partially crosslinked dimethyl polysiloxane composition (Note 1) | 3 |
| 3. | Alkyl/silicone-branched polyether-modified silicone (Note 2) | 2 |
| 4. | Decamethylcyclopentasiloxane | 20 |
| 5. | Diphenylsiloxy phenyl trimethicone (Note 3) | 5.5 |
| 6. | Triethylhexanoin | 5 |
| 7. | 2-Ethylhexyl p-methoxycinnamate | 7.5 |
| 8. | Octocrylene | 2.5 |
| 9. | Hexyl 2-[4-(diethylamino)-2-hydroxybenzoyl]benzoate | 1 |
| 10. | Hybrid silicone composite powder (Note 4) | 0.5 |
| 11. | Fine-particle titanium oxide dispersion (Note 5) | 5 |

-continued

| | (Ingredients) | Mass (%) |
|---|---|---|
| 12. | Fine-particle zinc oxide dispersion (Note 6) | 10 |
| 13. | 1,3-Butylene glycol | 2 |
| 14. | Ethanol | 6 |
| 15. | Sodium citrate | 0.2 |
| 16. | Sodium chloride | 0.5 |
| 17. | Purified water | balance |
| | Total | 100 |

(Note 1)
Phenyl-modified partially crosslinked dimethyl polysiloxane composition; KSG-18A <crosslinked portion: 10 to 20%, diphenylsiloxy phenyl trimethicone: 80 to 90%> (manufactured by Shin-Etsu Chemical Co., Ltd.)
(Note 2)
Alkyl/silicone-branched polyether-modified silicone; KF-6038 (manufactured by Shin-Etsu Chemical Co., Ltd.)
(Note 3)
Diphenylsiloxy phenyl trimethicone; KF-56A (manufactured by Shin-Etsu Chemical Co., Ltd.)
(Note 4)
Hybrid silicone composite powder; KSP-100 (manufactured by Shin-Etsu Chemical Co., Ltd.)
(Note 5)
Fine-particle titanium oxide dispersion; SPD-T5 (manufactured by Shin-Etsu Chemical Co., Ltd.)
(Note 6)
Fine-particle zinc oxide dispersion; SPD-Z5 (manufactured by Shin-Etsu Chemical Co., Ltd.)

<Preparation of Cosmetic>
A: The ingredients 1 to 8 were uniformly mixed.
B: The ingredients 11 to 17 were uniformly mixed.
C: The mixture B was added to the mixture A and emulsified, and the ingredients 9, 10 were added thereto and uniformly mixed. Thus, a W/O sunscreen milk was obtained.

The obtained W/O sunscreen milk was not sticky, spread smoothly, provided refreshing feeling on use without powdery feeling, and also had favorable water resistance and cosmetic durability.

[Example 5] W/O Sunscreen Milk

| | (Ingredients) | Mass (%) |
|---|---|---|
| 1. | Polymer (I) solution in D5 (20 mass %) | 2 |
| 2. | Partially crosslinked polyether-modified silicone composition (Note 1) | 3 |
| 3. | Partially crosslinked dimethyl polysiloxane composition (Note 2) | 2 |
| 4. | Silicone-branched polyether-modified silicone (Note 3) | 1 |
| 5. | Dimethyl polysiloxane (6 cs) | 5 |
| 6. | Decamethylcyclopentasiloxane | 3 |
| 7. | Isotridecyl isononanoate | 4 |
| 8. | Fine-particle titanium oxide dispersion (Note 4) | 25 |
| 9. | Fine-particle zinc oxide dispersion (Note 5) | 35 |
| 10. | Dipropylene glycol | 2 |
| 11. | Sodium citrate | 0.2 |
| 12. | Sodium chloride | 1 |
| 13. | Purified water | balance |
| | Total | 100 |

(Note 1)
Partially crosslinked polyether-modified silicone composition; KSG-210 <crosslinked portion: 2 to 30%, dimethyl polysiloxane (6 cs): 70 to 80%> (manufactured by Shin-Etsu Chemical Co., Ltd.)
(Note 2)
Partially crosslinked dimethyl polysiloxane composition; KSG-15 <crosslinked portion: 4 to 10%, decamethylcyclopentasiloxane: 90 to 96%> (manufactured by Shin-Etsu Chemical Co., Ltd.)
(Note 3)
Silicone-branched polyether-modified silicone; KF-6028 (manufactured by Shin-Etsu Chemical Co., Ltd.)
(Note 4)
Fine-particle titanium oxide dispersion; SPD-T5 (manufactured by Shin-Etsu Chemical Co., Ltd.)
(Note 5)
Fine-particle zinc oxide dispersion; SPD-Z5 (manufactured by Shin-Etsu Chemical Co., Ltd.)

<Preparation of Cosmetic>
A: The ingredients 1 to 7 were uniformly mixed.
B: The ingredients 10 to 13 were uniformly mixed.
C: The mixture B was added to the mixture A and emulsified, and the ingredients 8, 9 were added thereto and uniformly mixed. Thus, a W/O sunscreen milk was obtained.

The obtained W/O sunscreen milk was not sticky, spread smoothly, provided refreshing feeling on use without powdery feeling, and also had favorable water resistance and cosmetic durability.

[Example 6] W/O Cream Foundation

| | (Ingredients) | Mass (%) |
|---|---|---|
| 1. | Alkyl-modified, partially crosslinked polyether-modified silicone composition (Note 1) | 3.5 |
| 2. | Alkyl-modified, partially crosslinked dimethyl polysiloxane composition (Note 2) | 5 |
| 3. | Alkyl-branched, polyether-modified silicone (Note 3) | 3 |
| 4. | Organic-modified clay mineral | 1.3 |
| 5. | Decamethylcyclopentasiloxane | 20 |
| 6. | 2-Ethylhexyl p-methoxycinnamate | 7.5 |
| 7. | Polymer (I) solution in D5 (20 mass %) | 2 |
| 8. | Hybrid silicone composite powder (Note 4) | 2 |
| 9. | Triethylhexanoin | 7 |
| 10. | Acrylic-silicone graft copolymer (Note 5) | 0.2 |
| 11. | Silicone-treated titanium oxide (Note 6) | 8.5 |
| 12. | Silicone-treated yellow iron oxide (Note 6) | q.s. |
| 13. | Silicone-treated red iron oxide (Note 6) | q.s. |
| 14. | Silicone-treated black iron oxide (Note 6) | q.s. |
| 15. | 1,3-Butylene glycol | 5 |
| 16. | Methyl parahydroxybenzoate | 0.15 |
| 17. | Sodium citrate | 0.2 |
| 18. | Sodium chloride | 0.5 |
| 19. | Purified water | balance |
| | Total | 100 |

(Note 1)
Alkyl-modified, partially crosslinked polyether-modified silicone composition (KSG-330 <crosslinked portion: 15 to 25%, triethylhexanoin: 75 to 85%>: manufactured by Shin-Etsu Chemical Co., Ltd.)
(Note 2)
Alkyl-modified, partially crosslinked dimethyl polysiloxane composition; KSG-43 <crosslinked portion: 25 to 35%, triethylhexanoin: 65 to 75%> (manufactured by Shin-Etsu Chemical Co., Ltd.)
(Note 3)
Alkyl-branched, polyether-modified silicone; KF-6048 (manufactured by Shin-Etsu Chemical Co., Ltd.)
(Note 4)
Hybrid silicone composite powder; KSP-100 (manufactured by Shin-Etsu Chemical Co., Ltd.)
(Note 5)
Acrylic-silicone graft copolymer; KP-578 (manufactured by Shin-Etsu Chemical Co., Ltd.)
(Note 6)
Silicone-treated powder; silicone-treated powder whose particle surfaces were hydrophobized with MT-9909 (manufactured by Shin-Etsu Chemical Co., Ltd.)

<Preparation of Cosmetic>
A: The ingredients 9 to 14 were dispersed with a roll mill.
B: The ingredients 1 to 8 were uniformly mixed.
C: The ingredients 15 to 19 were uniformly mixed.
D: The mixture C was added to the mixture B and emulsified, and the dispersion A was added thereto. Thus, a W/O cream foundation was obtained.

The obtained W/O cream foundation was not sticky, spread lightly, and had excellent cosmetic durability without secondary adhesion.

[Example 7] W/O liquid foundation

| | (Indredients) | Mass (%) |
|---|---|---|
| 1. | Partially crosslinked polyether-modified silicone composition (Note 1) | 3.5 |
| 2. | Alkyl-branched, polyether-modified silicone (Note 2) | 3 |
| 3. | Phenyl-modified, partially crosslinked dimethyl polysiloxane composition (Note 3) | 5 |
| 4. | Organic-modified clay mineral | 1.5 |
| 5. | Diphenylsiloxy phenyl trimethicone (Note 4) | 9 |
| 6. | Decamethylcyclopentasiloxane | 15 |
| 7. | Isotridecyl isononanoate | 7.5 |
| 8. | Polymer (I) solution in D5 (20 mass %) | 1 |
| 9. | Metallic-soap-treated fine-particle titanium oxide (average primary particle diameter: 20 nm) | 5 |
| 10. | Silicone-treated titanium oxide (Note 5) | 6.5 |
| 11. | Silicone-treated yellow iron oxide (Note 5) | q.s. |
| 12. | Silicone-treated red iron oxide (Note 5) | q.s. |
| 13. | Silicone-treated black iron oxide (Note 5) | q.s. |
| 14. | Glycerin | 2 |
| 15. | Dipropylene glycol | 3 |
| 16. | Phenoxy ethanol | 0.2 |
| 17. | Sodium citrate | 0.2 |
| 18. | Sodium chloride | 0.5 |
| 19. | Purified water | balance |
| | Total | 100 |

(Note 1)
Partially crosslinked polyether-modified silicone composition; KSG-210 <crosslinked portion: 20 to 30%, dimethyl polysiloxane(6 cs): 70 to 80%> (manufactured by Shin-Etsu Chemical Co., Ltd.)
(Note 2)
Alkyl-branched, polyether-modified silicone; KF-6048 (manufactured by Shin-Etsu Chemical Co., Ltd.)
(Note 3)
Phenyl-modified, partially crosslinked dimethyl polysiloxane composition; KSG-18A <crosslinked portion: 10 to 20%, diphenyisiloxy phenyl trimethicone: 80 to 90%> (manufactured by Shin-Etsu Chemical Co., Ltd.)
(Note 4)
Diphenylsiloxy phenyl trimethicone; KF-56A (manufactured by Shin-Etsu Chemical Co., Ltd.)
(Note 5)
Silicone-treated powder; silicone-treated powder whose particle surfaces were hydrophobized with KT-9909 (manufactured by Shin-Etsu Chemical Co., Ltd.)

<Preparation of Cosmetic>
A: The ingredients 8 to 13 were dispersed with a roll mill.
B: The ingredients 1 to 7 were uniformly mixed.
C: The ingredients 14 to 19 were uniformly mixed.
D: The mixture C was added to the mixture B and emulsified, and the dispersion A was added thereto. Thus, a W/O liquid foundation was obtained.

The obtained W/O liquid foundation was not sticky, spread lightly, and had excellent cosmetic durability without secondary adhesion. This polymer also has a dispersant performance, so that the color spreadability was also favorable.

[Example 8] W/O Stick Foundation

| | (Ingredients) | Mass (%) |
|---|---|---|
| 1. | Partially crosslinked polyglycerin-modified silicone composition (Note 1) | 4 |
| 2. | Silicone/alkyl-branched polyether-modified silicone (Note 2) | 1.5 |
| 3. | Stearoyl inulin (Note 3) | 2 |
| 4. | Ceresin | 5.5 |
| 5. | Neopentyl glycol diethylhexanoate | 8 |
| 6. | Triethylhexanoin | 4 |
| 7. | Dimethyl polysiloxane (6 cs) | 11.5 |
| 8. | Polymethylsilsesquioxane (Note 4) | 1.5 |
| 9. | Polymer (I) solution in D5 (20 mass %) | 1 |
| 10. | Silicone-treated titanium oxide (Note 5) | 6.5 |
| 11. | Silicone-treated yellow iron oxide (Note 5) | q.s. |
| 12. | Silicone-treated red iron oxide (Note 5) | q.s. |
| 13. | Silicone-treated black iron oxide (Note 3) | q.s. |
| 14. | Lecithin | 0.2 |
| 15. | Polyoxyethylenesorbitan monooleate (20 E.O.) | 0.3 |
| 16. | Dipropylene glycol | 5 |
| 17. | Methyl parahydroxybenzoate | 0.1 |
| 18. | Purified water | balance |
| | Total | 100 |

(Note 1)
Partially crosslinked polyglycerin-modified silicone composition; KSG-710 <crosslinked portion: 20 to 30%, dimethyl polysiloxane (6 cs): 70 to 80%> (manufactured by Shin-Esu Chemical Co., Ltd.)
(Note 2)
Silicone/alkyl-branched polyethel-modified silicone; KF-6038 (manufactured by Shin-Etsu Chemical Co., Ltd.)
(Note 3)
Stearoyl inulin; Rheopearl ISK2 (manufactured by Chiba Flour Milling Co., Ltd.)
(Note 4)
Polymethylsilsesquioxane; KMP-590 (manufactured by Shin-Etsu Chemical Co., Ltd.)
(Note 5)
Silicone-treated powder; silicone-treated powder whose particle surfaces were hydrophobized with KF-9909 (manufactured by Shin-Etsu Chemical Co., Ltd.)

<Preparation of Cosmetic>
A: The ingredients 10 to 15 were dispersed with a roll mill.
B: The ingredients 1 to 9 were heated to 95° C. and uniformly mixed.
C: The dispersion A and the ingredients 16 to 18 were uniformly mixed and heated to 85° C.
D: The mixture C was added to the mixture B, emulsified, filled into a stick-shaped container, and then gradually cooled. Thus, a W/O stick foundation was obtained.

The obtained W/O stick foundation was not sticky, spread lightly, and had excellent cosmetic durability without secondary adhesion.

[Example 9] Lipstick

| | (Ingredients) | Mass (%) |
|---|---|---|
| 1. | Polyethylene | 7 |
| 2. | Microcrystalline wax | 3 |
| 3. | Silicone wax (Note 1) | 10.5 |
| 4. | Triethylhexanoin | 15.5 |
| 5. | Neopentyl glycol diethylhexanoate | 14 |
| 6. | Neopentyl glycol dicaprate | 7 |
| 7. | Hydrogenated polyisobutene | balance |
| 8. | Diphenyl dimethicone (Note 2) | 7.5 |
| 9. | Sericite | 0.7 |
| 10. | Red No. 201 | q.s. |
| 11. | Red No. 202 | q.s. |

-continued

| | (Ingredients) | Mass (%) |
|---|---|---|
| 12. | Yellow No. 4 | q.s. |
| 13. | Silicone-treated titanium oxide (Note 3) | 2.7 |
| 14. | Silicone-treated black iron oxide (Note 3) | q.s. |
| 15. | Silicone-treated red iron oxide (Note 3) | q.s. |
| 16. | Polyglyceryl-2 triisostearate | 4 |
| 17. | Mica | 6 |
| 18. | Polymer (I) solution in D5 (20 mass %) | 1 |
| | Total | 100 |

(Note 1)
Silicone wax; KP-561P (manufactured by Shin-Etsu Chemical Co., Ltd.)
(Note 2)
Diphenyl dimethicone; KF-54HV (manufactured by Shin-Etsu Chemical Co., Ltd.)
(Note 3)
Silicone-treated powder; silicone-treated powder whose particle surfaces were hydrophobized with KF-574 (manufactured by Shin-Etsu Chemical Co., Ltd.)

<Preparation of Cosmetic>
A: The ingredients 9 to 16 were dispersed with a roll mill.
B: The ingredients 1 to 8 were heated to 95° C. and uniformly mixed.
C: The dispersion A, the mixture B, and the ingredients 17 to 18 were uniformly mixed and heated to 85° C.
D: The mixture C was filled into a stick-shaped container. Thus, a lipstick was obtained.

It was found that the obtained lipstick was neither sticky nor greasy, and had favorable cosmetic durability without oozing, secondary adhesion, and so forth.

[Example 10] Eye Cream

| | (Ingredients) | Mass (%) |
|---|---|---|
| 1. | Silicone/alkyl-modified, partially crosslinked polyether-modified silicone composition (Note 1) | 4 |
| 2. | Silicone/alkyl-modified, partially crosslinked dimethyl polysiloxane composition (Note 2) | 6 |
| 3. | Silicone/alkyl-branched polyether-modified silicone (Note 3) | 0.5 |
| 4. | Squalane | 12 |
| 5. | Jojoba oil | 5 |
| 6. | Polymer (I) solution in D5 (20 mass %) | 2 |
| 7. | Hybrid silicone composite powder (Note 4) | 2 |
| 8. | 1,3-Butylene glycol | 7 |
| 9. | Phenoxy ethanol | 0.25 |
| 10. | Sodium citrate | 0.2 |
| 11. | Sodium chloride | 0.5 |
| 12. | Purified water | balance |
| | Total | 100 |

(Note 1) Silicone/alkyl-modified partially crosslinked polyether-modified silicone composition; KSG-350Z <crosslinked portion: 20 to 30%, cyclopentasiloxane: 70 to 80%>: (manufactured by Shin-Etsu Chemical Co., Ltd.)
(Note 2) Silicone/alkyl-modified, partially crosslinked dimethyl polysiloxane composition; KSG-045Z <crosslinked portion: 15 to 25%, cyclopentasiloxane: 75 to 85%> (manufactured by Shin-Etsu Chemical Co., Ltd.)
(Note 3) Silicone/alkyl-branched polyether-modified silicone; KF-6038 (manufactured by Shin-Etsu Chemical Co., Ltd.)
(Note 4) Hybrid silicone composite powder; KSP-100 (manufactured by Shin-Etsu Chemical Co., Ltd.)

<Preparation of Cosmetic>
A: The ingredients 1 to 7 were uniformly mixed.
B: The ingredients 8 to 12 were uniformly mixed.
C: The mixture B was added to the mixture A and emulsified. Thus, an eye cream was obtained.

It was found that the obtained eye cream was neither sticky nor greasy, had dry touch, spread smoothly, and was able to keep tension.

[Example 11] Wrinkle Concealer

| | (Ingredients) | Mass (%) |
|---|---|---|
| 1. | Partially crosslinked polyether-modified silicone composition (Note 1) | 5 |
| 2. | Partially crosslinked dimethyl polysiloxane composition (Note 2) | 55 |
| 3. | Partially crosslinked dimethyl polysiloxane composition (Note 3) | 15 |
| 4. | Decamethylcyclopentasiloxane | balance |
| 5. | Highly polymerized dimethyl polysiloxane/D5 mixed solution (Note 4) | 5 |
| 6. | Polymer (II) solution in D5 (20 mass %) | 1 |
| 7. | Hybrid silicone composite powder (Note 5) | 12 |
| | Total | 100 |

(Note 1) Partially crosslinked polyether-modified silicone composition; KSG-210 <crosslinked portion: 20 to 30%, dimethyl polysiloxane (6 CS): 70 to 80%> (manufactured by Shin-Etsu Chemical Co., Ltd.)
(Note 2) Partially crosslinked dimethyl polysiloxane composition; KSG-15 <crosslinked portion: 4 to 10%, decamethylcyclopentasiloxane: 90 to 96%> (manufactured by Shin-Etsu Chemical Co., Ltd.)
(Note 3) Partially crosslinked dimethyl polysiloxane composition; KSG-16 <crosslinked portion: 20 to 30%, dimethyl polysiloxane (6 CS): 70 to 80%> (manufactured by Shin-Etsu Chemical Co., Ltd.)
(Note 4) Highly polymerized dimethyl polysiloxane/D5 mixed solution; KF-9028 (manufactured by Shin-Etsu Chemical Co., Ltd.)
(Note 5) Hybrid silicone composite powder; KSP-101 (manufactured by Shin-Etsu Chemical Co., Ltd.)

<Preparation of Cosmetic>
A: The ingredients 1 to 6 were uniformly mixed.
B: The ingredient 7 was added to the mixture A and uniformly mixed. Thus, a wrinkle concealer was obtained.

It was found that the obtained wrinkle concealer was neither sticky nor greasy, had dry touch, spread smoothly, and was able to retain the sealing effect.

[Example 12] W/O sunscreen cream

| | (Ingredients) | Mass (%) |
|---|---|---|
| 1. | Alkyl-modified, partially crosslinked polyglycerin-modified silicone composition (Note 1) | 3 |
| 2. | Alkyl-modified, partially crosslinked dimethyl polysiloxane composition (Note 2) | 3 |
| 3. | Silicone/alkyl-branched polyglycerin-modified silicone (Note 3) | 1.5 |
| 4. | Diphenylsiloxy phenyl trimethicone (Note 4) | 12 |
| 5. | 2-Ethylhexyl p-methoxycinnamate | 6 |
| 6. | Octyl salicylate | 1 |
| 7. | Hybrid silicone composite powder (Note 5) | 2 |
| 8. | Polymer (I) solution in D5 (20 mass %) | 2 |
| 9. | Xanthan gum | 0.3 |
| 10. | Dipropylene glycol | 5 |
| 11. | Glycerin | 3 |
| 12. | Methyl parahydroxybenzoate | 0.1 |
| 13. | Sodium citrate | 0.2 |
| 14. | Sodium chloride | 0.5 |
| 15. | Purified water | balance |
| | Total | 100 |

(Note 1) Alkyl-modified, partially crosslinked polyglycerin-modified silicone composition; KSG-840 <crosslinked portion: 25 to 35%, squalane: 65 to 75%> (manufactured by Shin-Etsu Chemical Co., Ltd.)
(Note 2) Alkyl-modified, partially crosslinked dimethyl polysiloxane composition; KSG-43 <crosslinked portion: 25 to 35%, triethylhexanoin: 65 to 75%> (manufactured by Shin-Etsu Chemical Co., Ltd.)

-continued

| (Ingredients) | Mass (%) |
|---|---|

(Note 3) Silicone/alkyl-branched polyglycerin-modified silicone; KF-6105 (manufactured by Shin-Etsu Chemical Co., Ltd.)
(Note 4) Diphenylsiloxy phenyl trimethicone; KF-56A (manufactured by Shin-Etsu Chemical Co., Ltd.)
(Note 5) Hybrid silicone composite powder; KSP-100 (manufactured by Shin-Etsu Chemical Co., Ltd.)

<Preparation of Cosmetic>
A: The ingredients 1 to 8 were uniformly mixed.
B: The ingredients 9 to 15 were uniformly mixed.
C: The mixture B was added to the mixture A and emulsified. Thus, a W/O sunscreen cream was obtained.

The obtained W/O sunscreen cream was not sticky, spread smoothly, provided refreshing feeling on use without greasiness, and also had favorable water resistance and cosmetic durability.

[Example 13] O/W sunscreen cream

|  | (Ingredients) | Mass (%) |
|---|---|---|
| 1. | Carboxy vinyl polymer | 0.3 |
| 2. | Ethanol | 10 |
| 3. | 1,3-Butylene glycol | 6 |
| 4. | Methyl parahydroxybenzoate | 0.1 |
| 5. | Sodium acrylate/sodium acryloyldimethyl taurate copolymer composition (Note 1) | 2 |
| 6. | Purified water | balance |
| 7. | Polymer (I) solution in D5 (20 mass %) | 0.5 |
| 8. | Diphenylsiloxy phenyl trimethicone (Note 2) | 3 |
| 9. | Partially crosslinked dimethyl polysiloxane composition (Note 3) | 1 |
| 10. | Cetanol | 2 |
| 11. | 2-Ethylhexyl p-methoxycinnamate | 5 |
| 12. | 2,4-bis-[{4-(2-ethylhexyloxy)-2-hydroxy}-phenyl]-6-(4-methoxyphenyl)-1,3,5-triazine | 1 |
| 13. | Polyoxyethylene (60) hydrogenated castor oil | 1 |
| 14. | Polyether-modified silicone (Note 4) | 0.5 |
| 15. | Sodium hydroxide 10% aqueous solution | q.s. |
|  | Total | 100 |

(Note 1) Sodium acrylate/sodium acryloyldimethyl taurate copolymer composition; SIMULGEL EG <crosslinked portion: 35 to 40%>: manufactured by SEPPIC)
(Note 2) Diphenylsiloxy phenyl trimethicone; KF-56A (manufactured by Shin-Etsu Chemical Co., Ltd.)
(Note 3) Partially crosslinked dimethyl polysiloxane composition; KSG-016F <crosslinked portion: 20 to 30%, dimethyl polysiloxane (6 cs): 70 to 80%> (manufactured by Shin-Etsu Chemical Co., Ltd.)
(Note 4) Polyether-modified silicone; KF-6011 (manufactured by Shin-Etsu Chemical Co., Ltd.)

<Preparation of Cosmetic>
A: The ingredients 1 to 6 were heated to 70° C. and uniformly mixed.
B: The ingredients 7 to 14 were heated to 70° C. and uniformly mixed.
C: The mixture B was added to the mixture A, emulsified, and then gradually cooled. The ingredient 15 was added thereto and uniformly mixed. Thus, an O/W sunscreen cream was obtained.

The obtained O/W sunscreen cream was not sticky, spread smoothly, provided refreshing feeling on use without greasiness, and also had favorable water resistance and cosmetic durability.

[Example 14] Mousse Cheek

|  | (Ingredients) | Mass (%) |
|---|---|---|
| 1. | Partially crosslinked dimethyl polysiloxane composition (Note 1) | 28 |
| 2. | Decamethylcyclopentasiloxane | balance |
| 3. | Neopentyl glycol diisostearate | 9 |
| 4. | Stearoyl inulin (Note 2) | 10 |
| 5. | Amorphous silicic anhydride (Note 3) | 0.5 |
| 6. | Polymer (I) solution in D5 (20 mass %) | 2 |
| 7. | Silicone-treated titanium oxide (Note 4) | 0.2 |
| 8. | Red No. 202 | q.s. |
| 9. | Silicone-treated yellow iron oxide (Note 4) | q.s. |
| 10. | Silicone-treated black iron oxide (Note 4) | q.s |
| 11. | Silicone-treated mica (Note 4) | 5.4 |
| 12. | Silicone-treated sericite (Note 4) | 10 |
|  | Total | 100 |

(Note 1) Partially crosslinked dimethyl polysiloxane composition; KSG-16 <crosslinked portion: 20 to 30%, dimethyl polysiloxane (6 cs): 70 to 80%> (manufactured by Sin-Etsu Chemical Co., Ltd.)
(Note 2) Stearoyl inulin; Rheopearl KL2 (manufactured by Chiba Flour Milling Co., Ltd.)
(Note 3) Amorphous silicic anhydride; AEROSIL 200 (manufactured by Nippon Aerosil Co., Ltd.)
(Note 4) Silicone-treated powder; silicone-treated powder whose particle surfaces were hydrophobized with KF-9909 (manufactured by Shin-Etsu Chemical Co., Ltd.)

<Preparation of Cosmetic>
A: The ingredients 1 to 6 were heated to 80° C. and uniformly mixed.
B: The ingredients 7 to 12 were uniformly mixed with a Henschel mixer.
C: The mixture B was added to the mixture A and gradually cooled. Thus, a mousse cheek was obtained.

The obtained mousse cheek was neither sticky nor greasy, spread smoothly, and had excellent adhesiveness and favorable cosmetic durability, too.

[Example 15] Jell Eye Color

|  | (Ingredients) | Mass (%) |
|---|---|---|
| 1. | Partially crosslinked dimethyl polysiloxane composition (Note 1) | 10.5 |
| 2. | Squalane | 17 |
| 3. | Dextrin palmitate (Note 2) | 8.5 |
| 4. | Isotridecyl isononanoate | balance |
| 5. | Polymer (I) solution in D5 (20 mass %) | 2 |
| 6. | Amorphous silicic anhydride (Note 3) | 0.1 |
| 7. | Hybrid silicone composite powder (Note 4) | 5 |
| 8. | Barium sulfate | 9 |
| 9. | Silicone-treated mica (Note 5) | 32.5 |
|  | Total | 100 |

(Note 1) Partially crosslinked dimethyl polysiloxane composition; KSG-16 <crosslinked portion: 20 to 30%, dimethyl polysiloxane (6 cs): 70 to 80%> (manufactured by Shin-Etsu Chemical Co., Ltd.)
(Note 2) Dextrin palmitate; Rheopearl KL2 (manufactured by Chiba Flour Milling Co., Ltd.)
(Note 3) Amorphous silicic anhydride; AEROSIL 972 (manufactured by Nippon Aerosil Co., Ltd.)
(Note 4) Hybrid silicone composite powder; KSP-100 (manufactured by Shin-Etsu Chemical Co., Ltd.)
(Note 5) Silicone-treated powder; silicone-treated powder whose particle surfaces were hydrophobized with KP-574 (manufactured by Shin-Etsu Chemical Co., Ltd.)

<Preparation of Cosmetic>
A: The ingredients 1 to 5 were heated to 80° C. and uniformly mixed.
B: The ingredient 6 to 9 were added to the mixture A, heated to 90° C., and uniformly mixed.
C: The mixture B was poured into a container. Thus, a jell eye color was obtained.

The obtained jell eye color spread smoothly, was neither greasy nor powdery, and also had favorable cosmetic durability.

[Example 16] Powder foundation

| | (Ingredients) | Mass (%) |
|---|---|---|
| 1. | 2-Ethylhexyl p-methoxycinnamate | 4 |
| 2. | Diphenylsiloxy phenyl trimethicone (Note 1) | 4.5 |
| 3. | Triethylhexanoin | 1.5 |
| 4. | Silicone/alkyl-branched polyglycerin-modified silicone (Note 2) | 0.6 |
| 5. | Polymer (I) solution in D5 (20 mass %) | 1 |
| 6. | Silicone-treated mica (Note 3) | 30 |
| 7. | Barium sulfate | 10 |
| 8. | Phenyl-modified hybrid silicone composite powder (Note 4) | 5 |
| 9. | Polymethylsilsesquioxane (Note 5) | 4 |
| 10. | Silicone-treated talc (Note 3) | balance |
| 11. | Silicone-treated titanium oxide (Note 3) | 6 |
| 12. | Silicone-treated yellow iron oxide (Note 3) | q.s |
| 13. | Silicone-treated red iron oxide (Note 3) | q.s. |
| 14. | Silicone-treated black iron oxide (Note 3) | q.s. |
| | Total | 100 |

(Note 1) Diphenylsiloxy phenyl trimethicone; KF 56A (manufactured by Shin-Etsu Chemical Co., Ltd.)
(Note 2) Silicone/alkyl-branched polyglycerin-modified silicone; KF-6105 (manufactured by Shin-Etsu Chemical Co., Ltd.)
(Note 3) Silicone-treated powder; silicone-treated powder whose particle surfaces were hydrophobized with KP-574 (manufactured by Shin-Etsu Chemical Co., Ltd.)
(Note 4) Phenyl-modified hybrid silicone composite powder; KSP-300 (manufactured by Shin-Etsu Chemical Co., Ltd.)
(Note 5) Polymethylsilsesquioxane; KMP-590 (manufactured by Shin-Etsu Chemical Co., Ltd.)

<Preparation of Cosmetic>
A: The ingredients 1 to 4 were uniformly mixed.
B: The ingredients 5 to 14 were uniformly mixed.
C: The mixture A was added to the mixture B and uniformly mixed with a Henschel mixer. The obtained powder was passed through a mesh, followed by molding in a metal dish using a mold. Thus, a powder foundation was obtained.

The obtained powder foundation spread lightly and had favorable cosmetic durability without secondary adhesion.

[Example 17] Outbath hair treatment

| | (Ingredients) | Mass (%) |
|---|---|---|
| 1. | Partially crosslinked polyether-modified silicone composition (Note 1) | 3 |
| 2. | Partially crosslinked dimethyl polysilioxane composition (Note 2) | 1 |
| 3. | Polyether-modified silicone (Note 3) | 0.2 |
| 4. | Dimethyl polysiloxane (6 CS) | 8 |
| 5. | Fragrance | q.s. |
| 6. | Polymer (I) solution in isododecane (30 mass %) | 1 |
| 7. | Dipropylene glycol | 8 |
| 8. | Ethanol | 5 |
| 9. | Methyl parahydroxybenzoate | 0.1 |
| 10. | Sodium citrate | 0.2 |
| 11. | Sodium chloride | 0.5 |
| 12. | Purified water | balance |
| | Total | 100 |

(Note 1) Partially crosslinked polyether-modified silicone composition; KSG-210 <crosslinked portion: 20 to 30%, dimethyl polysiloxane (6 CS): 70 to 80%> (manufactured by Shin-Etsu Chemical Co., Ltd.)
(Note 2) Partially crosslinked dimethyl polysiloxane composition; KSG-19 <crosslinked portion: 10 to 20%, decamethylcyclopentasiloxane: 80 to 90%> (manufactured by Shin-Etsu Chemical Co., Ltd.)
(Note 3) Polyether-modified silicone; KF 6017 (manufactured by Shin-Etsu Chemical Co., Ltd.)

<Preparation of Cosmetic>
A: The ingredients 1 to 4 were uniformly mixed.
B: The ingredients 7 to 12 were uniformly mixed.
C: The mixture B was added to the mixture A and emulsified, and the ingredients 5, 6 were added thereto. Thus, an outbath treatment was obtained.

It was found that the obtained outbath hair treatment spread smoothly and made the hair glossy and smooth.

[Example 18] Hair treatment

| | (Ingredients) | Mass (%) |
|---|---|---|
| 1. | Polymer (I) solution in isododecane (30 mass %) | 0.5 |
| 2. | Cetanol | 2 |
| 3. | Cetyl octanoate | 3 |
| 4. | Behentrimonium chloride | 1 |
| 5. | Butyl parahydroxybenzoate | 0.1 |
| 6. | Diphenylsiloxy phenyl trimethicone Note 1) | 1 |
| 7. | Propylene glycol | 5 |
| 8. | Hydroxyethylcellulose | 0.1 |
| 9 | Purified water | balance |
| 10. | Amino-modified silicone emulsion (Note 2) | 4 |
| 11. | Fragrance | q.s. |
| | Total | 100 |

(Note 1) Diphenylsiloxy pheny trimethicone; KF-56A (manufactured by Shin-Etsu Chemical Co., Ltd.)
(Note 2) Amino-modified silicone emulsion; X-52-2328 (manufactured by Shin-Etsu Chemical Co., Ltd.)

<Preparation of Cosmetic>
A: The ingredients 1 to 7 were heated to 70° C. and uniformly mixed.
B: The ingredients 8, 9 were heated to 70° C. and uniformly mixed.
C: The mixture B was added to the mixture A, emulsified, and gradually cooled. Then, the ingredients 10, 11 were added thereto. Thus, a treatment was obtained.

It was found that the obtained hair treatment spread smoothly and made the hair glossy and smooth.

[Example 19] Hair oil

| | (Ingredients) | Mass (%) |
|---|---|---|
| 1. | Polymer (II) solution in isododecane (20 mass %) | 2 |
| 2. | Diphenylsiloxy phenyl trimethicone (Note 1) | 7 |
| 3. | Diethylhexyl succinate | 10 |
| 4. | Highly polymerized dimethyl polysiloxane mixed solution (Note 2) | 2 |
| 5. | Tocopherol | 0.1 |
| 6. | Fragrance | 0.1 |
| 7. | Hydrogenated polyisobutene | balance |
| | Total | 100 |

(Note 1) Diphenylsiloxy phenyl trimethicone; KF-56A (manufactured by Shin-Etsu Chemical Co., Ltd.)
(Note 2) Highly polymerized dimethyl polysiloxane mixed solution; KF-9030 (manufactured by Shin-Etsu Chemical Co., Ltd.)

<Preparation of Cosmetic>
A: The ingredients 1 to 7 were uniformly mixed. Thus, a hair oil was obtained.

It was found that the obtained hair oil spread smoothly and made the hair glossy and smooth.

[Example 20] Hair Wax

| | (Ingredients) | Mass (%) |
|---|---|---|
| 1. | Polymer (I) solution in isododecane (30 mass %) | 1 |
| 2. | Methyl trimethicone (Note 1) | 10 |
| 3. | Candelilla wax | 14 |
| 4. | Microcrystalline wax | 6 |
| 5. | POE glyceryl isostearate | 2 |
| 6. | Glycerin monostearate | 3 |
| 7. | Polyether-modified silicone (Note 2) | 2 |
| 8. | Stearic acid | 2 |
| 9. | 2-Ethylhexyl p-methoxycinnamate | 0.1 |
| 10. | Propylene glycol | 6 |
| 11. | 1,3-Butylene glycol | 6 |
| 12. | Carboxy vinyl polymer | 0.3 |
| 13. | Methyl parahydroxybenzoate | 0.2 |
| 14. | Phenoxy ethanol | 0.3 |
| 15. | Trisodium edetate | q.s. |
| 16. | Purified water | balance |
| 17. | Potassium hydroxide (10% solution) | q.s. |
| 18. | Fragrance | q.s. |
| | Total | 100 |

(Note 1) Methyl trimethicone; TMF-1.5 (manufactured by Shin-Etsu Chemical Co., Ltd.)
(Note 2) Polyether-modified silicone; KF-6011 (manufactured by Shin-Etsu Chemical Co., Ltd.)

<Preparation of Cosmetic>
A: The ingredients 10 to 16 were heated to 80° C. and uniformly mixed.
B: The ingredients 1 to 9 were heated to 90°C and uniformly mixed.
C: The mixture B was added to the mixture A, emulsified, and then cooled to room temperature.
D: The ingredients 17, 18 were added to the emulsion C and uniformly mixed. Thus, a hair wax was obtained.

It was found that the obtained hair wax was little sticky and favorably retained holding force and antiperspirant effect.

[Example 21] Oil-Based Mascara

| | (Ingredients) | Mass (%) |
|---|---|---|
| 1. | Polymer (I) solution in isododecane (30 mass %) | 12 |
| 2. | Trimethylsiloxysilicate solution in isododecane (Note 1) | 8 |
| 3. | Dextrin palmitate (Note 2) | 2 |
| 4. | Paraffin wax | 6 |
| 5. | Microcrystalline wax | 7 |
| 6. | Isododecane | 30 |
| 7. | Organic-modified clay mineral | 5.5 |
| 8. | Silicone-treated black iron oxide (Note 3) | 5 |
| 9. | Silicone-treated talc (Note 3) | 5 |
| 10. | Hybrid silicone composite powder (Note 4) | 5 |
| 11. | Polyether-modified silicone (Note 5) | 1.2 |
| 12. | Propylene carbonate | 1.6 |
| 13. | Methyl parahydroxybenzoate | 0.1 |
| 14. | Isododecane | balance |
| | Total | 100 |

(Note 1) Trimethylsiloxysilicate solution; X-21-5595 (manufactured by Shin-Etsu Chemical Co., Ltd.)
(Note 2) Dextrin palmitate; Rheopearl TL2 (manufactured by Chiba Flour Milling Co., Ltd.)
(Note 3) Silicone-treated powder; silicone-treated powder whose particle surfaces were hydrophobized with KF-9909 (manufactured by Shin-Etsu Chemical Co., Ltd.)
(Note 4) Hybrid silicone composite powder; KSP-105 (manufactured by Shin-Etsu Chemical Co., Ltd.)
(Note 5) Polyether-modified silicone; KF-6017 (manufactured by Shin-Etsu Chemical Co., Ltd.)

<Preparation of Cosmetic>
A: The ingredients 1 to 6 were heated to 95° C. and uniformly mixed.
B: The mixture A and the ingredient 7 to 14 were heated to 90° C. and uniformly mixed.
C: The mixture B was gradually cooled. Thus, an oil-based mascara was obtained.

It was found that the obtained oil-based mascara had favorable finish, cosmetic durability, and holding force. Moreover, the use in combination with such a hard and brittle film formed from trimethylsiloxysilicate, such a soft film formed from silicone-modified acrylic polymer, and the like can adjust film performances and feeling on use such as finish.

[Example 22] W/O oil-based mascara

| | (Ingredients) | Mass (%) |
|---|---|---|
| 1. | Polymer (I) solution in isododecane (30 mass %) | 10 |
| 2. | Acrylic-silicone graft copolymer solution in isododecane (Note 1) | 10 |
| 3. | Dextrin palmitate/ethylhexanoate (Note 2) | 3 |
| 4. | Silicone wax (Note 3) | 2 |
| 5. | Ceresin | 2.5 |
| 6. | Beeswax | 4.5 |
| 7. | Diphenylsiloxy phenyl trimethicone (Note 4) | 3 |
| 8. | Isododecane | balance |
| 9. | Organic-modified clay mineral | 4 |
| 10. | Silicone-treated black iron oxide (Note 5) | 5 |
| 11. | Silicone-treated talc (Note 5) | 4.5 |
| 12. | Amorphous silicic anhydride (Note 6) | 2.7 |
| 13. | Silicone-branched polyether-modified silicone (Note 7) | 1 |
| 14. | Propylene carbonate | 1.3 |
| 15. | Phenoxy ethanol | 0.2 |
| 16. | 1,3-Butylene glycol | 1 |
| 17. | Purified water | 12.8 |
| | Total | 100 |

(Note 1) Acrylic-silicone graft copolymer solution; KP 550 (manufactured by Shin-Etsu Chemical Co., Ltd.)
(Note 2) Dextrin palmitate/ethylhexanoate); Rheopearl TT2 (manufactured by Chiba Flour Milling Co., Ltd.)
(Note 3) Silicone wax; KP-562P (manufactured by Shin-Etsu Chemical Co., Ltd.)
(Note 4) Diphenylsiloxy phenyl trimethicone; KF-56A (manufactured by Shin-Etsu Chemical Co., Ltd.)
(Note 5) Silicone-treated powder; silicone-treated powder whose particle surfaces were hydrophobized with KF-9909 (manufactured by Shin-Etsu Chemical Co., Ltd.)
(Note 6) Amorphous silicic anhydxide; AEROSIL 972 (manufactured by Nippon Aerosoil Co., Ltd.)
(Note 7) Silicone-branched polyether-modified silicone; KF-6028 (manufactured by Shin-Etsu Chemical Co., Ltd.)

<Preparation of Cosmetic>
A: The ingredients 1 to 8 were heated to 95°C and uniformly mixed.
B: The mixture A and the ingredients 9 to 14 were heated to 85° C. and uniformly mixed.
C: The ingredients 15 to 17 were heated to 85° C. and uniformly mixed.
D: The mixture C was added to the mixture B, emulsified, and then gradually cooled. Thus, a W/O oil-based mascara was obtained.

It was found that the obtained W/O oil-based mascara had favorable finish, cosmetic durability, and holding force. Moreover, the use in combination with such a hard and brittle film formed from trimethylsiloxysilicate, such a soft film formed from silicone-modified acrylic polymer, and the like can adjust film performances and feeling on use such as finish.

[Example 23] Antiperspirant

|   | (Ingredients) | Mass (%) |
|---|---|---|
| 1. | Partially crosslinked polyether-modified silicone composition (Note 1) | 7 |
| 2. | Polymer (I) solution in D5 (20 mass %) | 8 |
| 3. | Decamethylcyclopentasiloxane | 9 |
| 4. | 1,3-Butylene glycol | 5 |
| 5. | Sodium citrate | 0.2 |
| 6. | Glycine salt of aluminum zirconium tetrachloride hydrate | 20 |
| 7. | Purified water | balance |
|   | Total | 100 |

(Note 1) Partially crosslinked polyether-modified silicone composition; KSG-210 <cross-linked portion: 20 to 30%, dimethyl polysiloxane (6 CS): 70 to 80%> (manufactured by Shin-Etsu Chemical Co., Ltd.)

<Preparation of Cosmetic>
A: The ingredients 1 to 3 were uniformly mixed.
B: The ingredients 4 to 7 were uniformly mixed.
C: Under stirring, the mixture B was slowly added to the mixture A and emulsified. Thus, an antiperspirant was obtained.

It was found that the obtained antiperspirant spread smoothly and favorably retained antiperspirant effect without whitening the skin.

[Example 24] Nail Enamel Overcoat

|   | (Ingredients) | Mass (%) |
|---|---|---|
| 1. | Polymer (II) solution 10 isododecane (20 mass %) | 9 |
| 2. | Nitrocellulose | 17 |
| 3. | Alkyd resin | 4 |
| 4. | Acetyl triethyl citrate | 5 |
| 5. | Butyl acetate | 29 |
| 6. | Ethyl acetate | 25 |
| 7. | Isopropyl alcohol | 3 |
| 8. | n-Butyl alcohol | 1 |
| 9. | Toluene | balance |
|   | Total | 100 |

<Preparation of Cosmetic>
A: The ingredients 5 to 9 were mixed, and the ingredient 4 was added thereto and uniformly mixed.
B: The ingredients 1 to 3 were added to the mixture A and mixed. Thus, a nail enamel overcoat was obtained.

It was found that the obtained enamel overcoat spread smoothly, had the enamel more glossy, and was durable.

It should be noted that the present invention is not restricted to the above-described embodiments. The embodiments are merely examples, and any embodiments that have substantially the same feature and demonstrate the same functions and effects as those in the technical concept as disclosed in claims of the present invention are included in the technical scope of the present invention.

The invention claimed is:
1. A cosmetic comprising an organosiloxane graft polyvinyl alcohol polymer comprising: a structural unit shown by the following general formula (1), and a structural unit shown by the following general formula (3),
wherein the cosmetic comprises the organosiloxane graft polyvinyl alcohol polymer in an amount of 0.01 to 20 mass% relative to the total amount of the cosmetic,
wherein the organosiloxane graft polyvinyl alcohol polymer has a number average molecular weight (Mn) of 5,000 to 500,000 as measured by GPC in terms of polystyrene,

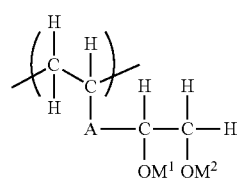

wherein $M^1$ and $M^2$ each represent a hydrogen atom, an acetyl group, or a siloxane group shown by the following general formula (2), provided that at least one of $M^1$ and $M^2$ is a siloxane group shown by the general formula (2); and A represents a single bond,

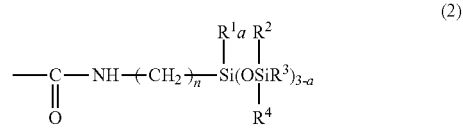

wherein $R^1$ represents a monovalent organic group having 1 to 6 carbon atoms; $R^2$, $R^3$, and $R^4$ each represent a monovalent organic group having 1 to 6 carbon atoms or a siloxy group shown by $-OSiR^5R^6R^7$, where $R^5$, $R^6$, and $R^7$ each represent a monovalent organic group having 1 to 6 carbon atoms; "n" represents an integer of 1 to 10; and "a" represents an integer of 0 to 2,

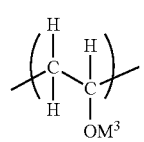

wherein $M^3$ represents a hydrogen atom, an acetyl group, or a siloxane group shown by the general formula (2).

2. The cosmetic according to claim 1, wherein in the general formula (2), "n" is 3, $R^2$, $R^3$, and $R^4$ are methyl groups, and "a" is 0.

3. The cosmetic according to claim 1, wherein the organosiloxane graft polyvinyl alcohol polymer is a reaction product of a (butenediol/vinyl alcohol) copolymer and tris(trimethylsiloxy)silylpropyl isocyanate.

4. The cosmetic according to claim 2, wherein the organosiloxane graft polyvinyl alcohol polymer is a reaction product of a (butenediol/vinyl alcohol) copolymer and tris(trimethylsiloxy)silylpropyl isocyanate.

* * * * *